US008048415B2

(12) United States Patent
Moser et al.

(10) Patent No.: US 8,048,415 B2
(45) Date of Patent: *Nov. 1, 2011

(54) COMPOSITIONS AND METHODS FOR PROMOTING OR INHIBITING ANGIOGENESIS

(75) Inventors: Tammy L. Moser, Durham, NC (US); Salvatore V. Pizzo, Bahama, NC (US); Mary S. Stack, Chicago, IL (US)

(73) Assignees: Duke University, Durham, NC (US); Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/538,952

(22) Filed: Aug. 11, 2009

(65) Prior Publication Data

US 2010/0040675 A1 Feb. 18, 2010

Related U.S. Application Data

(63) Continuation of application No. 11/403,607, filed on Apr. 13, 2006, now Pat. No. 7,595,047, which is a continuation of application No. 09/862,798, filed on May 22, 2001, now abandoned, which is a continuation-in-part of application No. 09/314,159, filed on May 19, 1999, now Pat. No. 6,444,431.

(60) Provisional application No. 60/124,070, filed on Mar. 12, 1999, provisional application No. 60/086,155, filed on May 19, 1998.

(51) Int. Cl.
*A61K 39/395* (2006.01)
*A61K 39/00* (2006.01)
*C07K 16/28* (2006.01)
*C12P 21/08* (2006.01)

(52) U.S. Cl. ............... 424/130.1; 424/133.1; 424/138.1; 424/141.1; 424/143.1; 530/387.1; 530/387.3; 530/388.1; 530/388.22

(58) Field of Classification Search .................. None
See application file for complete search history.

(56) References Cited

U.S. PATENT DOCUMENTS

| | | |
|---|---|---|
| 5,086,164 A | 2/1992 | Maione et al. |
| 5,112,946 A | 5/1992 | Maione |
| 5,284,827 A | 2/1994 | Maione et al. |
| 5,512,591 A | 4/1996 | Halperin et al. |
| 5,593,664 A | 1/1997 | Wright et al. |
| 5,639,725 A | 6/1997 | O'Reilly et al. |
| 5,681,372 A | 10/1997 | Magits |
| 5,744,492 A | 4/1998 | Kohn et al. |
| 5,786,150 A | 7/1998 | Hillman et al. |
| 5,837,682 A | 11/1998 | Folkman et al. |
| 5,945,403 A | 8/1999 | Folkman et al. |
| 6,024,688 A | 2/2000 | Folkman et al. |
| 6,025,353 A | 2/2000 | Masferrer |
| 6,056,973 A | 5/2000 | Allen et al. |
| 6,110,722 A | 8/2000 | Hillman et al. |
| 6,180,370 B1 * | 1/2001 | Queen et al. .................. 435/69.6 |
| 6,201,104 B1 | 3/2001 | MacDonald |
| 6,380,253 B1 | 4/2002 | Das |
| 6,387,371 B1 | 5/2002 | Hudziak et al. |
| 6,572,856 B1 | 6/2003 | Taylor et al. |
| 7,595,047 B2 * | 9/2009 | Moser et al. ............... 424/141.1 |

FOREIGN PATENT DOCUMENTS

| | | |
|---|---|---|
| WO | WO 99/59620 | 11/1999 |
| WO | WO 99/66038 | 12/1999 |
| WO | WO 00/32631 | 6/2000 |

OTHER PUBLICATIONS

Stryer et al, in Biochemistry, Third edition, W H Freeman Company, New York, pp. 31-33, 1998.*
Ngo et al., The Protein Folding Problem and Tertiary Structure Prediction, pp. 491-495, 1994.*
Chica et al, Curr Opin Biotechnol 16(4):378-84, Aug. 2005.*
Witkowski et al, Biochemistry 38(36): 11643-50, Sep. 7, 1999.*
Seffernick et al, J Bacteriol 183 (8): 2405-10, Apr. 2001.*
Stancoviski et al, PNAS; 88: 8691-8695, 1991.*
Jiang et al, J. Biol. Chem. 280 (6): 4656-4662, Feb. 11, 2005.*
Freshney Ri et al. Culture of Animal Cells, A Manual of Basic Technique. Alan R. Liss, Inc., 1983, New York, p. 4.
Dermer GB. Another anniversary for the war on cancer. Bio/Technology. Mar. 1994. 12: 320.
Gura T. Systems for identifying new drugs are often faulty. Science. Nov. 7, 1997; 278: 1041-1042.
Jain RK. Barriers to drug delivery in solid tumors. Scientific American. Jul. 1994; 271(1): 58-65.
Waldmann TA. Monoclonal antibodies in diagnosis and therapy. Science. Jun. 21, 1991; 252: 1657-1662.
Harris WJ and Emery S. Therapeutic antibodies—the coming of age. TIBTECH. Feb. 1993; 11: 42-44.

(Continued)

*Primary Examiner* — Phuong Huynh
(74) *Attorney, Agent, or Firm* — Myers Bigel Sibley & Sajovec, P.A.

(57) ABSTRACT

Compounds, compositions and methods for promoting or inhibiting angiogenesis, and screening methods for identifying compounds are disclosed. The compounds bind to F1 ATP synthase, particularly to the alpha and/or beta subunits of F1 ATP synthase. When bound to these subunits, they can function as angiostatin agonists, antagonists, partial agonists, inverse agonists, or allosteric modulators. When the compounds mimic or enhance the activity of angiostatin, they inhibit angiogenesis. When the compounds inhibit the ability of angiostatin to bind F1 ATP synthase and are either inactive at inhibiting angiogenesis or directly promote angiogenesis, or if they inhibit the activity of angiostatin, they promote angiogenesis. The compounds can be, for example, antibodies, antibody fragments, enzymes, peptides, nucleic acids such as oligonucleotides, or small molecules. The antibodies can be monoclonal, humanized, or polyclonal antibodies. The compounds can be conjugated to or combined with various cytotoxic agents and/or labeled compounds. Methods for promoting angiogenesis can be used to introduce vasculature to areas in a patient that can benefit from such increased vasculature. Methods for inhibiting angiogenesis can be used to treat disorders mediated by angiogenesis, for example, tumors, autoimmune disorders such as rheumatoid arthritis, and the like.

6 Claims, 14 Drawing Sheets

OTHER PUBLICATIONS

Amalfitano A and Parks RJ. Separating fact from fiction: assessing the potential of modified adenovirus vectors for use in human gene therapy. Current Gene Therapy. 2002; 2: 111-133.

Verma IM and Somia N. Gene therapy—promises, problems and prospects. Nature. Sep. 18, 1997; 389: 239-242.

The Department of Health and Human Services has released a memorandum dated Jan. 14, 2003. p. 1-3.

Pandha HS et al. Oncological applications of gene therapy. Current Opinions in Investigational Drugs. 2000; 1(1): 122-134.

Almus FE et al. Mechanism for diminished tissue factor expression by endothelial cells cultured with heparin binding growth factor-1 and heparin. Blood. Mar. 15, 1991; 77(6): 1256-1262.

Langer DJ et al. Regulation of the endothelial cell urokinase-type plasminogen activator receptor. Evidence for cyclic AMP-dependent and protein kinase C-dependent pathways. Circulation Research. Feb. 1993; 72(2): 330-340.

Kohn EC et al. Angiogenesis: role of calcium-mediated signal transduction. Proc. Natl. Acad. Sci. USA. Cell Biology. Feb. 1995. 92: 1307-1311.

Morisaki N. et al. Mechanism of angiogenic effects of saponin from Ginseng *Radix rubra* in human umbilical vein endothelial cells. British Journal of Pharmacology. 1995; 115: 1188-1193.

Griffioen AW et al. Tumor angiogenesis is accompanied by a decreased inflammatory response of tumor-associated endothelium. Blood. Jul. 15, 1996; 88(2): 667-673.

Malinda KM et al. Thymosin $\beta_4$ stimulates directional migration of human umbilical vein endothelial cells. FASEB J. May 1997; 11: 474-481.

Papapetropoulos A et al. Nitric oxide production contributes to the angiogenic properties of vascular endothelial growth factor in human endothelial cells. J. Clin. Invest. Dec. 1997; 100(12): 3131-3139.

Wang J et al. Effect of a novel inhibitory mAb against β-subunit of F1F0 ATPase on HCC. Cancer Biology & Therapy. Nov. 2008; 7(11): 1829-1835.

Genentech Inc., "Highlights of Prescribing Information, Herceptin," (2008).

Moser, et al., "Endothelial Cell Surface F1F0 ATP Synthesis and is Inhibited by Angiostatin," *Proc. Natl. Acad. Sci.* 98(12):6656-61 (2001).

Moser, et al., "Angiostatin Binds ATP Synthase on the Surface of Human Endothelial Cells," Proc. Natl. Acad. Sci. 96(12):2811-16 (1999).

Boyer, "The ATP Synthase—A Splendid Molecular Machine," *Annnu. Rev. Biochem.* 66:717-749 (1997).

Das, et al., "A Novel Ligand in Lymphocyte-mediated Cytotoxicity: Expression of the β Subunit of $H^+$Transporting ATP Synthase on the Surface of Tumor Cells Lines," *J. Exp. Med.* 180:273-281 (1994).

Dunn, et al., "Monoclonal Antibodies to *Escherichia coli* $F_1$-ATPase," *J. Biol. Chem.* 260:10418-10425 (1985).

Elston, et al., "Energy transduction ATP Synthase," Nature 39:510-513 (1998).

Feller, et al., "A monoclonal antibody detecting dipeptideylpeptidase IV in human tissue," *Virchos Arch. A. Pathol. Anata. Histopathol.* 409(2):263-273 (1986).

Gogol, et al., "Cryoelectron icroscopy of *escherichia coli* $F_1$ Adenosinetriphosphatase Decorated with monoclonal Antibodies to Individual Subunits of the Complex," *Biochem.* 28:4717-4724 (1989).

Hartel, et al., "Characterization of Different Forms of Dipeptidyl Peptidase IV from Rat Liver and Hepatoma by Monoclonal Antibodies," *Adv. Exp. Med. Biol.* 240:206-214 (1988).

Kataoka, et al., "Nucleotide sequence of a cDNA for the α subunit of human mitochondrial ATP Synthase," *Biochimica et Biophysica Acta* 1089:393-395 (1991).

Miles, et al., "Roley of Cell-Surface Lysines in Plasminogen Binding to Cells: Identification of α-Enolase as a Candidate Plasminogen Recepor," *Biochemistry* 30(6):1682-1691 (1991).

Moradi-Ameli, et al., "Chacterization of monoclonalantibodies against mitachondrial $F_1$-ATPase," *PNAS* 80:6167-6171 (1983).

Moreno, et al., "Vascular-type $H^+$-ATPase regi;ates cytoplasmic pH in Toxoplasma gondii tachyzoites," *Biochem. J.* 330:853-860 (1998).

Nelson, et al., "Immunochemical Analysis of the membrane Proteins of Rat Liver and Zajdela Hepatoma Mitochondria," *Arch. Biochem. Biophys.* 234:24-30 (1984).

Rao, et al., "The Defective Proton—ATPase of *uncA* Mutants of *Escherichia coli*: ATP-Binding an ATP-Induced Conformational Change in Mutant α-Subunits", *Archives of Biochemistry and Biophysics* 255(2):309-315 (1987).

\* cited by examiner

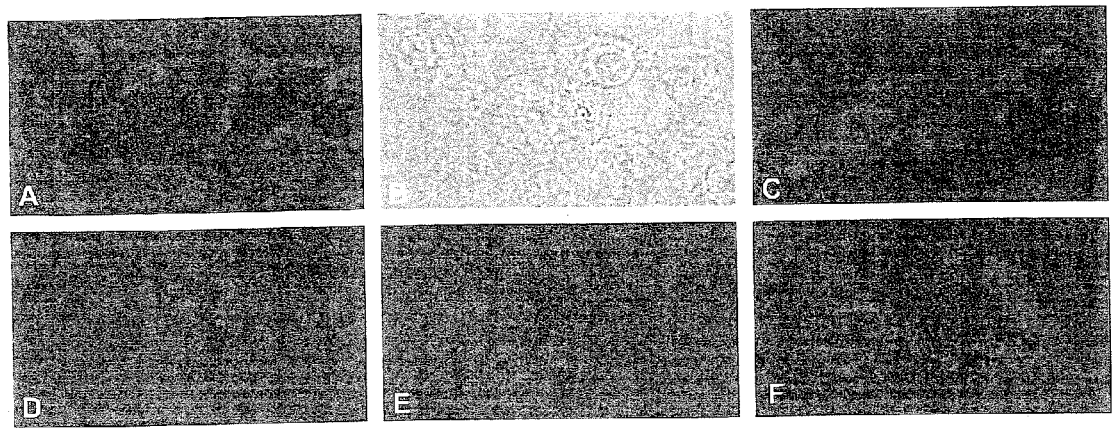
Figs. 5 A-F

COMPOSITIONS AND METHODS FOR PROMOTING OR INHIBITING ANGIOGENESIS

CROSS-REFERENCE TO RELATED APPLICATIONS

This application claims priority to and is a continuation of U.S. patent application Ser. No. 11/403,607, filed Apr. 13, 2006, now U.S. Pat. No. 7,595,047, which is a continuation of U.S. patent application Ser. No. 09/862,798, filed May 22, 2001, now abandoned, which is a continuation-in-part of U.S. patent application Ser. No. 09/314,159, filed May 19, 1999, now Pat. No. 6,444,431 which claims the benefit of U.S. Provisional patent application Ser. No. 60/086,155, filed May 19, 1998, and U.S. Provisional Patent Application Ser. No. 60/124,070, filed Mar. 12, 1999, the disclosures of all of which are incorporated by reference herein in their entirety.

FIELD OF THE INVENTION

This application is generally in the area of compositions and methods for promoting or inhibiting angiogenesis.

BACKGROUND OF THE INVENTION

Angiogenesis is the formation of new capillary blood vessels leading to neovascularization. Angiogenesis is a complex process which includes a series of sequential steps including endothelial cell-mediated degradation of vascular basement membrane and interstitial matrices, migration of endothelial cells, proliferation of endothelial cells, and formation of capillary loops by endothelial cells.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane.

Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, thereby creating the new blood vessel.

In normal physiological processes such as wound healing, angiogenesis is turned off once the process is completed. In contrast, tumor angiogenesis is not self-limiting. The progressive growth of solid tumors beyond clinically occult sizes (e.g., a few $mm^3$) requires the continuous formation of new capillary blood vessels to deliver nutrients and oxygen for the tumor itself to grow, a process known as tumor angiogenesis. Solid tumors elicit an angiogenic response in the surrounding normal tissue for further growth. The resultant neovascularization of the tumor is associated with more rapid growth, and local invasion. Therefore, either inhibition of tumor angiogenesis (antiangiogenic therapy) or selective destruction of a tumor's existing blood vessels (vascular targeting therapy) would suppress or arrest tumor growth and its spread.

Further, in certain pathological (and nonmalignant) processes, angiogenesis is abnormally prolonged. Examples include ocular neovascular disease, which is characterized by invasion of new blood vessels into the retina or cornea, as well as other eye-related diseases. Other angiogenesis-associated diseases include diabetic retinopathy and chronic inflammatory diseases such as rheumatoid arthritis, dermatitis and atherosclerosis.

Antiangiogenic therapy has been proposed for modulating such angiogenesis-associated disorders. One approach has been to administer VEGF (vascular endothelial growth factor) inhibitors. Other approaches involve using angiostatin or endostatin, which are both known to inhibit angiogenesis. The in vivo use of angiostatin or endostatin is somewhat limited by their relatively short half-lives in vivo.

It would be advantageous to have new antiangiogenic compositions and methods to add to the arsenal of therapies available for treating these angiogenesis-mediated disorders. It would also be advantageous to have new methods for identifying such compositions and methods. The present invention provides such compositions and methods.

SUMMARY OF THE INVENTION

The present invention is directed to compounds, compositions and methods for promoting or inhibiting angiogenesis, and results from the discovery that angiostatin binds to ATP synthase, in particular, to the alpha and beta subunits of F1 ATP synthase, and, when so bound, inhibits angiogenesis.

The compounds bind to F1 ATP synthase, particularly to the alpha and/or beta subunits of F1 ATP synthase. When bound to these subunits, they inhibit the ability of angiostatin to bind to the subunits, and can function as angiostatin agonists, antagonists, partial agonists, inverse agonists, or allosteric modulators. Compounds that mimic or enhance the activity of angiostatin inhibit angiogenesis. Compounds that are inactive at inhibiting angiogenesis, directly promote angiogenesis, or inhibit the activity of angiostatin promote angiogenesis.

The compounds can be, for example, antibodies, antibody fragments, enzymes, proteins, peptides, nucleic acids such as oligonucleotides, or small molecules. The antibodies can be, for example, monoclonal, humanized (chimeric) or polyclonal antibodies, and can be prepared, for example, using conventional techniques. The compounds can be conjugated to various cytotoxic agents and/or labeled compounds.

The compounds can be included in various compositions, for example, compositions suitable for intravenous, intramuscular, topical, local, intraperitoneal, or other forms of administration. They can be targeted to capillary beds by incorporating them into appropriately sized microparticles or liposomes that remain lodged in capillary beds and release the compounds at a desired location.

Methods for promoting angiogenesis can be used to introduce vasculature to areas in a patient that can benefit from such increased vasculature. Methods for inhibiting angiogenesis can be used to treat disorders mediated by angiogenesis, for example, tumors, autoimmune disorders such as rheumatoid arthritis, and the like. The methods involve administering effective amounts of suitable angiogenic or anti-angiogenic compounds and/or compositions including the compounds to patients in need of treatment. Effective angiogenic amounts are amounts effective to promote angiogenesis, and effective anti-angiogenic amounts are amounts effective to inhibit at least a significant amount of the angiogenesis that would otherwise occur in the absence of treatment.

Screening methods can be used to identify compounds useful in these methods. The screening methods can identify compounds that bind to F1 ATP synthase, and, in particular, the alpha and/or beta subunits, as well as determining the activity of the compounds once bound. Combinatorial libraries of compounds, for example, phage display peptide libraries, small molecule libraries and oligonucleotide libraries can be screened. Compounds that bind to F1 ATP synthase, in particular, to the alpha and/or beta subunits thereof, can be identified, for example, using affinity binding studies, or using other screening techniques known to those of skill in the art. The effect of the compounds once bound to the F1 ATP synthase or alpha and/or beta subunits thereof can be determined, for example, by evaluating the level of ATP synthesis, the proliferation of human vascular endothelial cells (HUVEC), the viability and, or growth of tumors, wound healing, Matrigel™ tube formation and corneal pocket in mouse or rat.

Nucleic acid sequences encoding F1 ATP synthase, or the alpha and/or beta subunits or portions thereof, and host cells transformed therewith, are also disclosed.

BRIEF DESCRIPTION OF THE DRAWINGS

FIG. 1A. $^{125}$I-labeled plasminogen binding was concentration-dependent and saturable with an apparent dissociation constant (Kalpha) of 158 nM and 870,000 sites/cell. FIG. 1B. Binding to HUVEC with $^{125}$I-labeled angiostatin was concentration-dependent and saturable with a Kd of 245 nM and 38,000 sites/cell. Error bars represent standard deviation.

(A) Total binding of 1.0 µM $^{125}$I-labeled plasminogen was designated as 100%.

(B) Plasminogen binding is inhibited by about 80% in the presence of a 25-fold molar excess of unlabeled plasminogen.

(C) Plasminogen binding was not inhibited in the presence of a 100-fold molar excess of unlabeled angiostatin suggesting distinct binding sites for each on the cells.

(D) showed no inhibition of binding in the presence of a 2-fold molar excess unlabeled plasminogen (E) Error bars represent standard deviation.

FIGS. 3A-3D. Affinity purification of plasminogen and angiostatin binding sites. SDS-PAGE containing membrane proteins were prepared and then analyzed by Western blotting. Membranes were incubated in 10 mM Tris-HCl, 0.15M NaCl, 0.05% NP40, pH 7.5 containing, FIG. 3A, streptavidin-alkaline phosphatase conjugate antibody, or, FIG. 3B, anti-annexin II antibody and developed using 5-bromo-4-chloroindol-yl-3-phosphate intro blue tetrazolium. Membrane stained with Coomassie Brilliant blue, FIG. 3C, showing affinity purified membrane proteins. Membrane incubated with $^{125}$I-labeled plasminogen, FIG. 3D, showing binding to the plasminogen purified membrane and not the angiostatin. Lane 1 represents protein eluted from the plasminogen-Sepharose column. Lane 2 represents protein eluted from the angiostatin-Sepharose column. The relative molecular weights of alpha-ATP synthase and beta-ATP synthase are about 59,800 Da and about 56,500 Da, respectively.

Figure 4A:
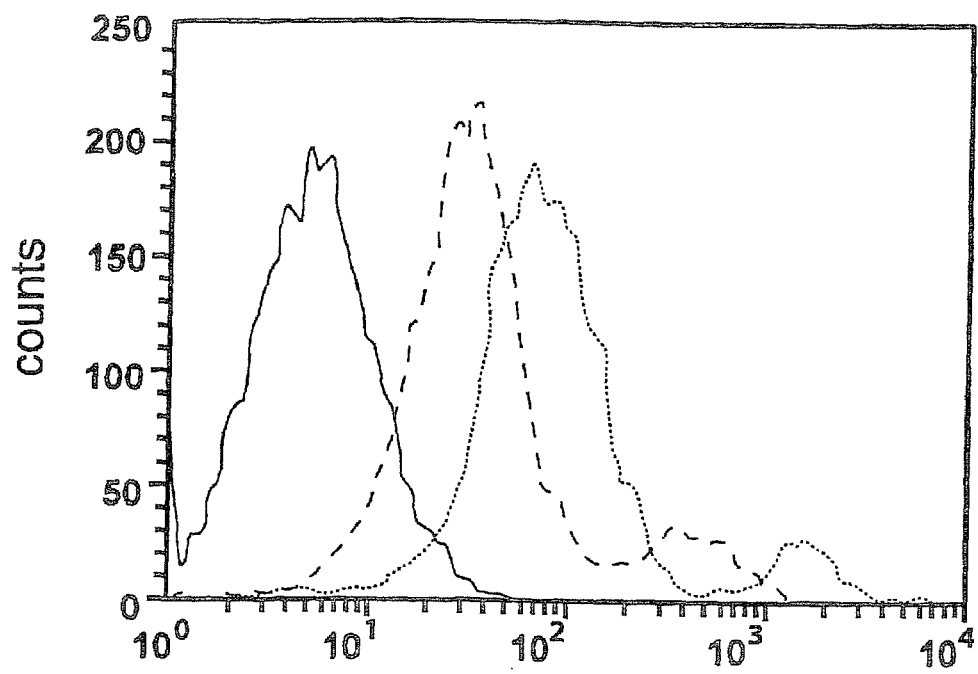
Figure 4B:
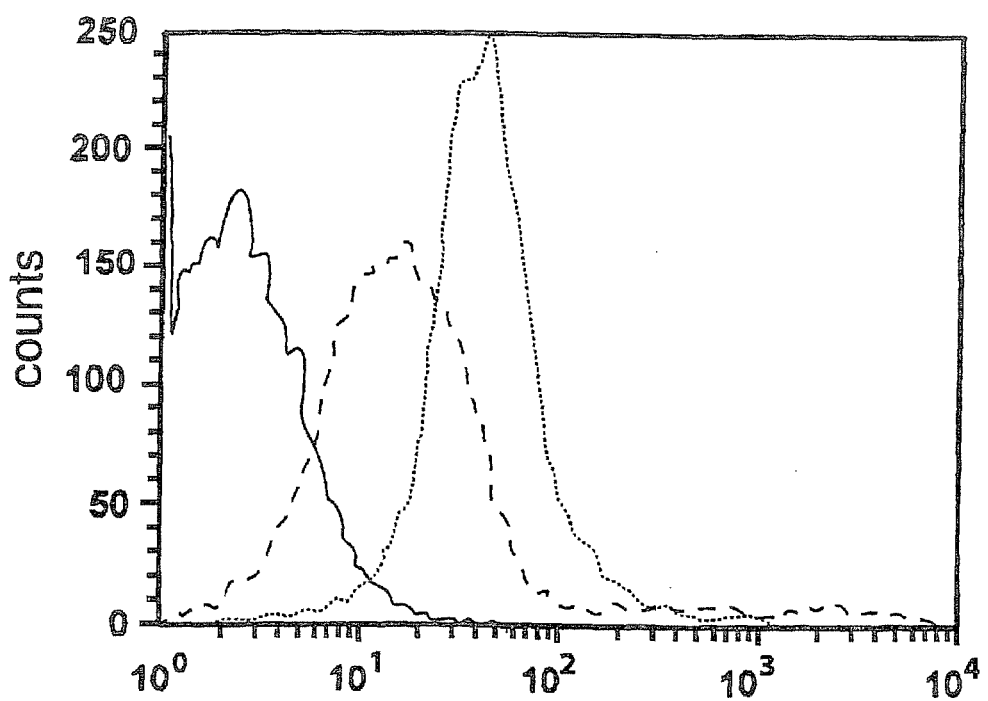
Figure 4C:
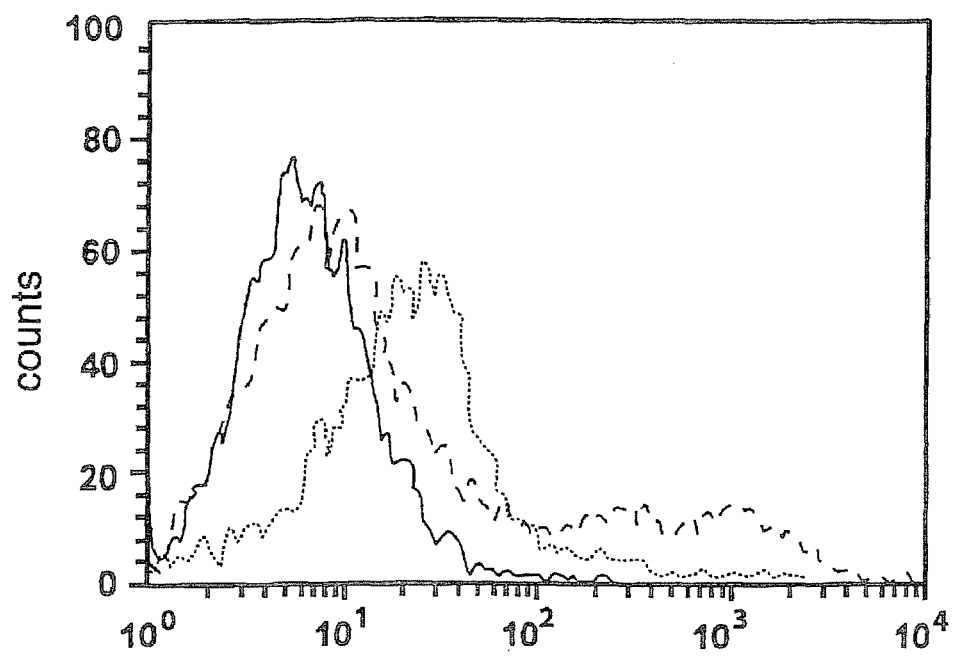

FIGS. 4A-4D. Binding of antibody directed against the alpha subunit of ATP synthase on the surface of HUVEC by flow cytometry. HUVEC were analyzed by FACScan Flow Cytometry. Histogram plots are shown for HUVEC (FIG. 4A) and A549 (FIG. 4B) where (-) represents cells incubated with antibody directed against the alpha subunit of ATP synthase, (---) pre-immune serum and (-) secondary antibody only. Histogram plot of A549 shown in FIG. 4C are similar with ('") representing antibody incubated with a 5-fold molar excess alpha ATP synthase protein.

Figure 4D:
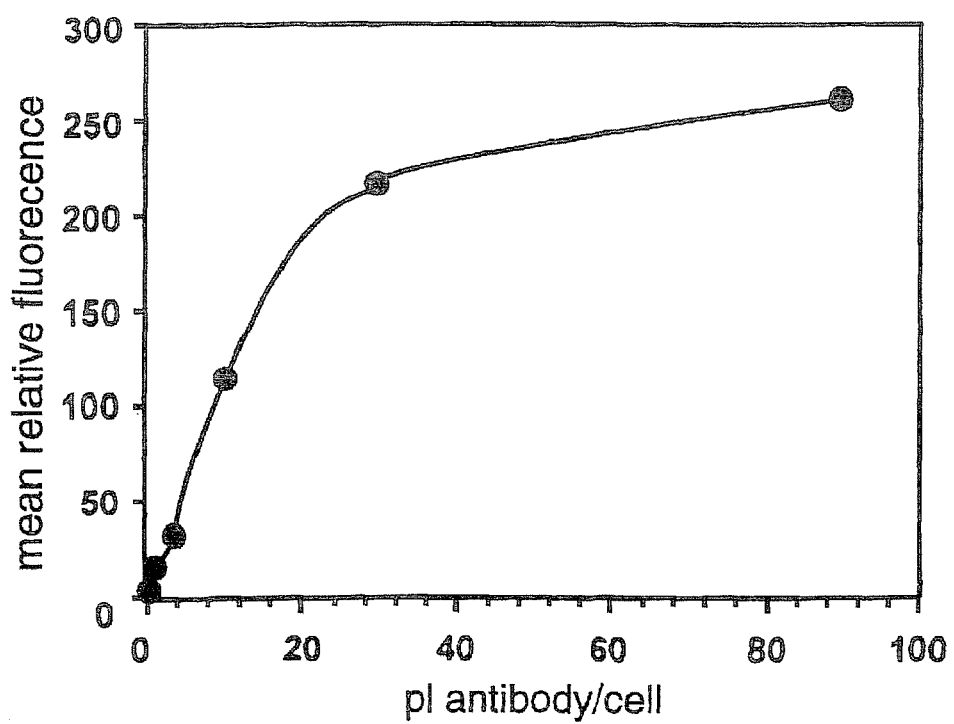

In FIG. 4D, HUVEC demonstrate specific, saturable binding of antibodies directed against the alpha subunit of ATP synthase. The mean relative fluorescence of HUVEC incubated with pre-immune rabbit serum subtracted from the mean relative fluorescence of HUVEC incubated with the same volume of anti-alpha ATP synthase gave the mean relative fluorescence resulting from the specific binding of antibodies directed against the alpha subunit of ATP synthase on the HUVEC surface.

FIGS. 5A-5F. Immunofluorescence microscopy of ATP-synthase on HUVEC surface. HUVEC were incubated with rabbit polyclonal anti-serum raised against the alpha subunit of ATP synthase from *E. coli*. FIG. 5A, HUVEC under epi-illumination showing immunofluorescent surface staining for the alpha subunit of ATP synthase. FIG. 5B, Same field of HUVEC under visible light.

FIG. 5C, Human dermal microvascular endothelial cells also showed immunofluorescent surface staining for the alpha subunit of ATP synthase. Control experiments were performed with FIG. 5D, pre-immune serum and FIG. 5E, secondary antibody alone. FIG. 5F, HUVEC were permeabilized by acetone fixation prior to adding antibodies for the alpha subunit of ATP synthase.

Figure 6:
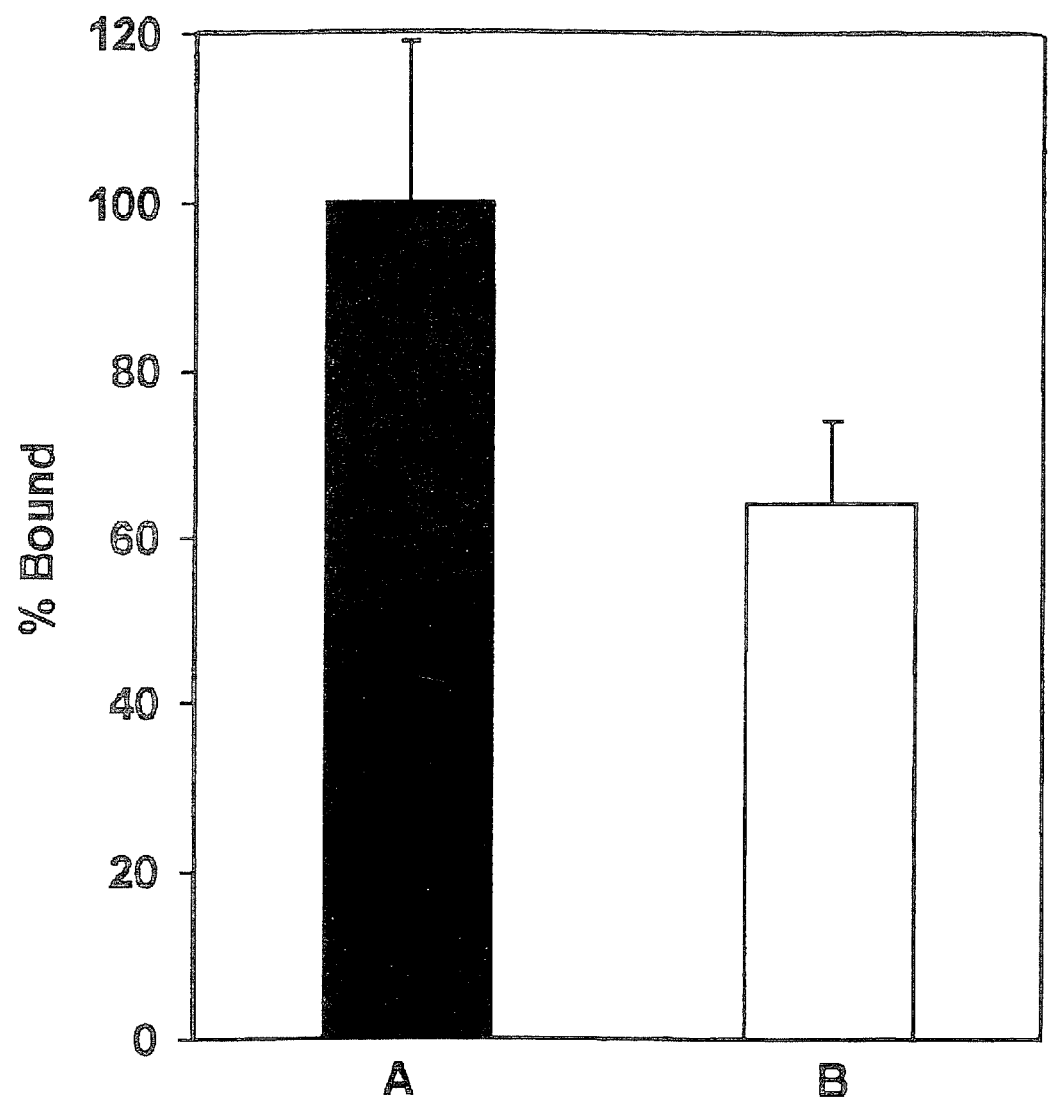

FIG. 6. Competition binding assay between angiostatin and the antibody against the alpha subunit of ATP synthase from *E. coli*. HUVEC were plated at a constant density of 10,000 cells/well and incubated with 0.5 µM $^{125}$I-labeled angiostatin in the presence of 1:10 dilution of antibody against the alpha subunit of ATP synthase from *E. coli* for 1 h at 4° C. Cells were washed and remaining bound radioactivity was quantified by γ-counting. Non-specific binding was measured in the presence of excess unlabeled angiostatin and was subtracted from total binding. (A) Total binding of 0.5 µM $^{125}$I-labeled angiostatin was designated as 100%. (B) Angiostatin binding is inhibited by 59% in the presence of a 1:10 dilution of anti-alpha subunit ATP synthase antibody. Competition studies were also performed simultaneously using rabbit pre-immune serum to account for non-specific inhibition. Error bars represent standard deviation. A 1 tailed homoscedastic t test was used for statistical analysis; p<0.10.

FIGS. 7A-7E. Angiostatin binding to the recombinant alpha subunit of human ATP synthase. The alpha subunit of human ATP synthase was cloned and expressed in *E. coli* and purified using Qiagen's nickel-Sepharose protein purification system before dialyzing in phosphate buffered saline (PBS), pH 7.0. Recombinant protein was electrophoresed on 5-15% SDS-PAGE, electroblotted onto Immobilon™ membrane and incubated 18 h in 10 mM Tris-HCl, 0.15M NaCl, 0.05% NP40, pH 7.5 (TSN) containing $^{125}$I-angiostatin. For competition studies, unlabeled ligand was added 4 h prior to radiolabeled ligand. Blots were washed in TSN buffer containing 0.05%/Tween80 and bound radioactivity was quantified on a Molecular Dynamics PhosphorImager™.

Figure 7:
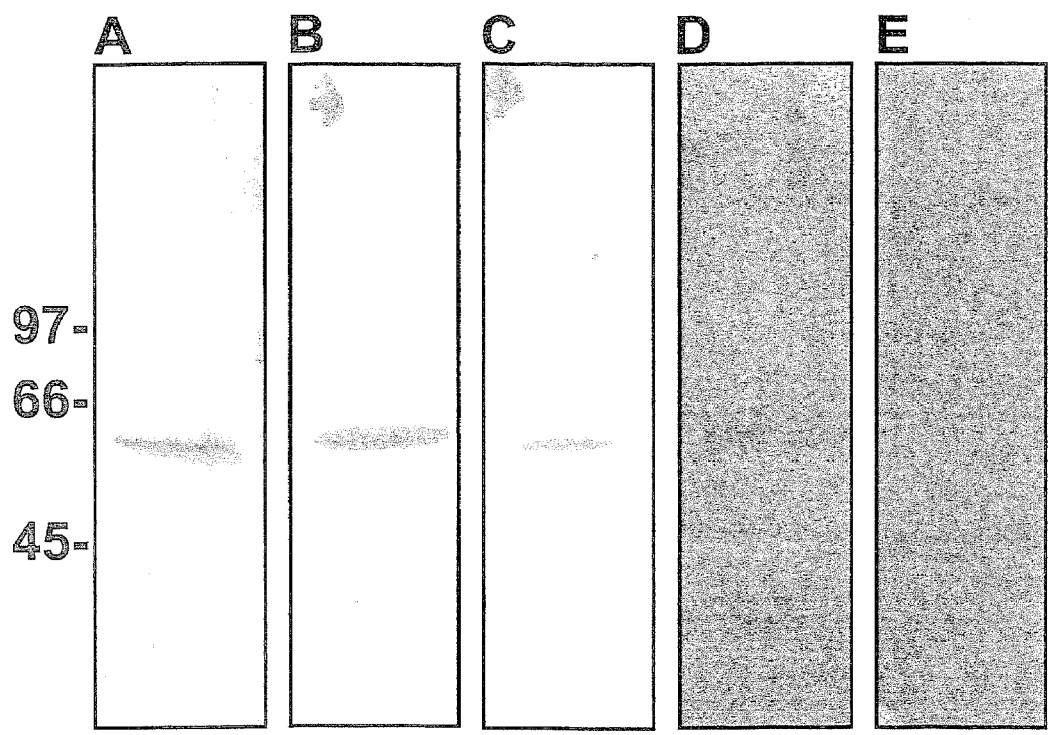

FIG. 7A. Coomassie stain of Immobilon membrane containing the alpha subunit of human-ATP synthase.

FIG. 7B. Binding of 0.5 mM $^{125}$I-labeled angiostatin.

FIG. 7C. Binding of 0.5 mM $^{125}$I-labeled angiostatin in the presence of a 250-fold molar excess of unlabeled angiostatin. Binding of angiostatin is inhibited by about 56%. FIG. 7D. Binding of 0.5 nM $^{125}$I-labeled angiostatin in the presence of a 2500-fold molar excess of unlabeled plasminogen. Binding of angiostatin is not inhibited. FIG. 7E. Binding of 0.5

Figure 3:
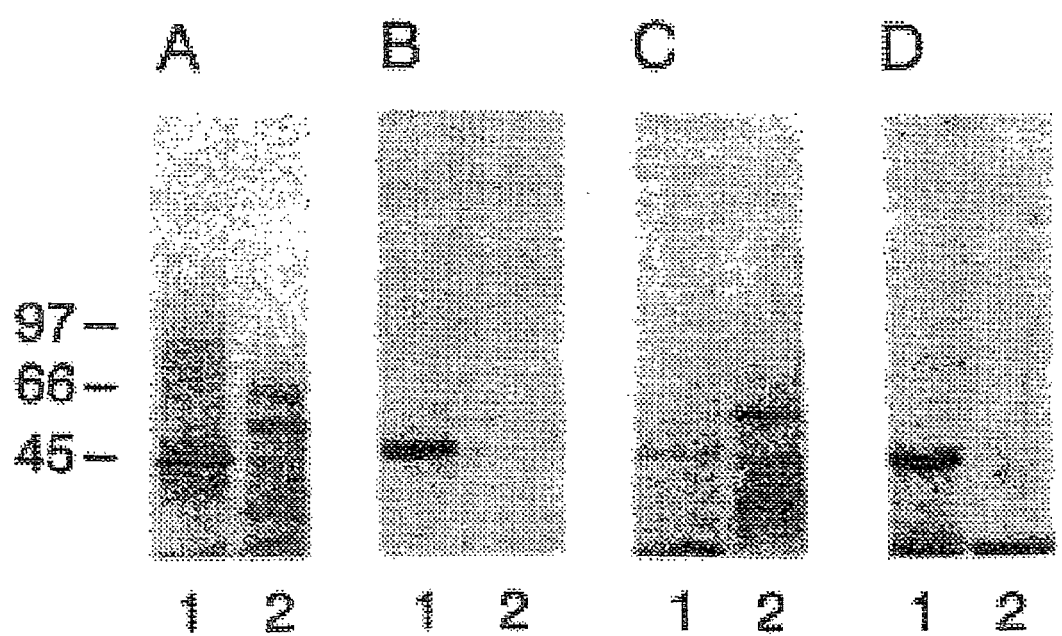

M $^{125}$I-labeled plasminogen to the alpha subunit of human ATP synthase. Plasminogen did not bind to the recombinant alpha subunit of ATP synthase, however, it did bind the annexin II control (as shown in FIG. 3).

Figure 8:
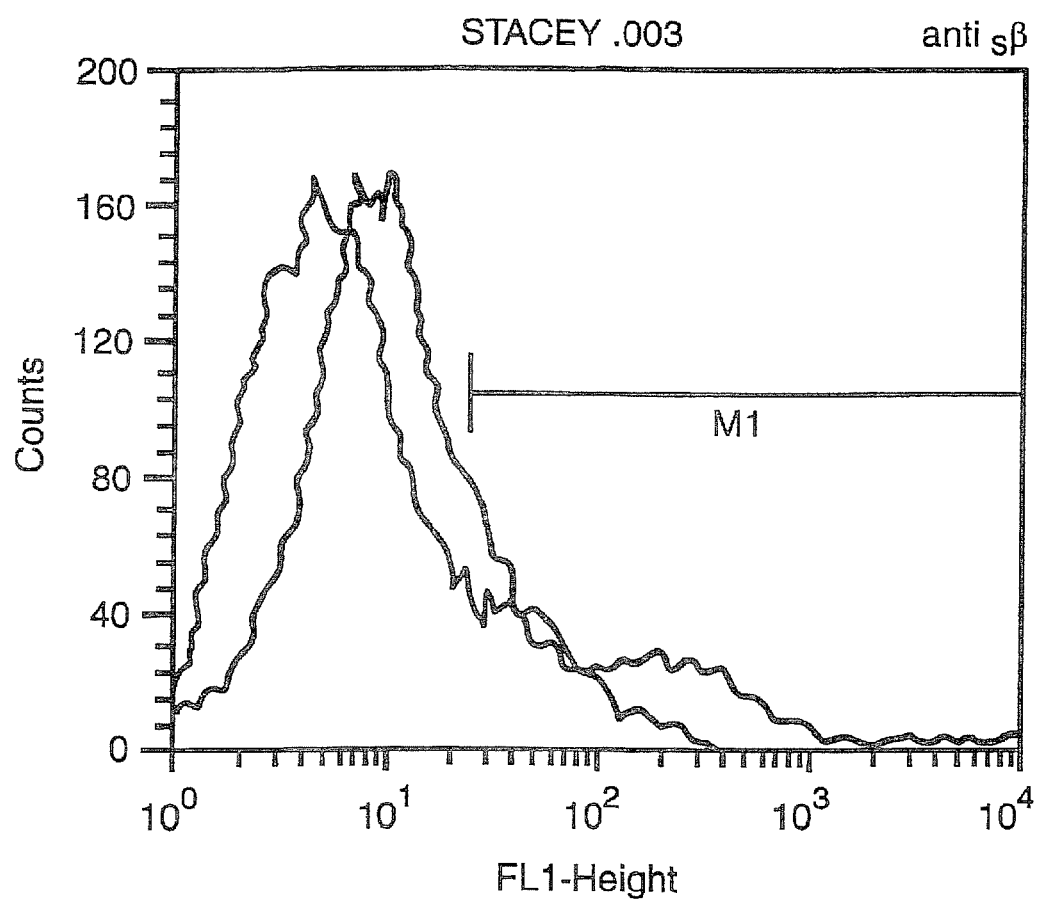

FIG. 8. Binding of antibody directed against the beta subunit of ATP synthase on the surface of HUVEC by flow cytometry. HUVEC were analyzed by FACscan Flow Cytometry as described above and in the examples. Histogram plots are shown for HUVEC cells incubated with antibody directed against the beta subunit of ATP synthase.

Figure 9:

FIG. 9 (a-d) are confocal micrographs showing the co-localization of the alpha- and beta-subunits of ATP synthase on the surface of HUVEC by immunostaining and confocal microscopy. 9a represents non-permeabilized HUVEC immunostained with a murine monoclonal antibody specific for the alpha-subunit of ATP synthase. 9b represents the same cells immunostained with a rabbit polyclonal antiserum specific for the beta-subunit of ATP synthase. 9c represents composite co-localization images obtained by digital overlays of the above images. 9d represents a co-localization image obtained from cells permeabilized with ethanol (100%). Representative images shown, n=26.

Figure 10:
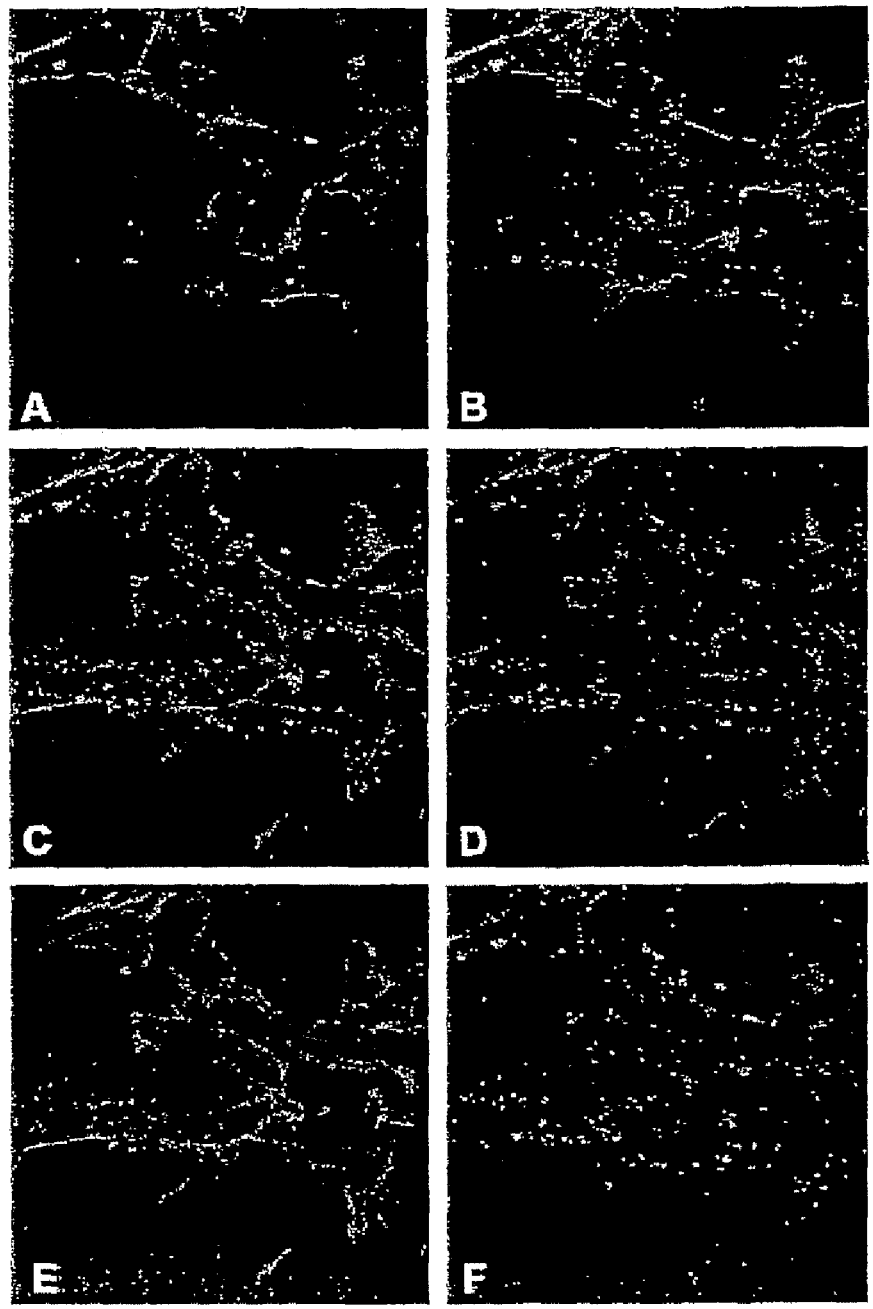

FIG. 10 (A-F) are confocal micrographs representing the surface localization of the alpha-subunits of ATP synthase and CD31 on non permeabilized HUVEC by immunostaining and confocal microscopy. Confocal optical sections were taken along the z-axis every 1.5 m. Each section is approximately 0.6 m in thickness. A series of z-sections from a representative field is shown, starting with the basal surface in Panel A and ending with the apical surface in Panel D. FIG. 10E shows the same section in panel C, with fluorescence from the red channel only. FIG. 10F shows the same section in panel C, with fluorescence from the green channel only.

Figure 11:
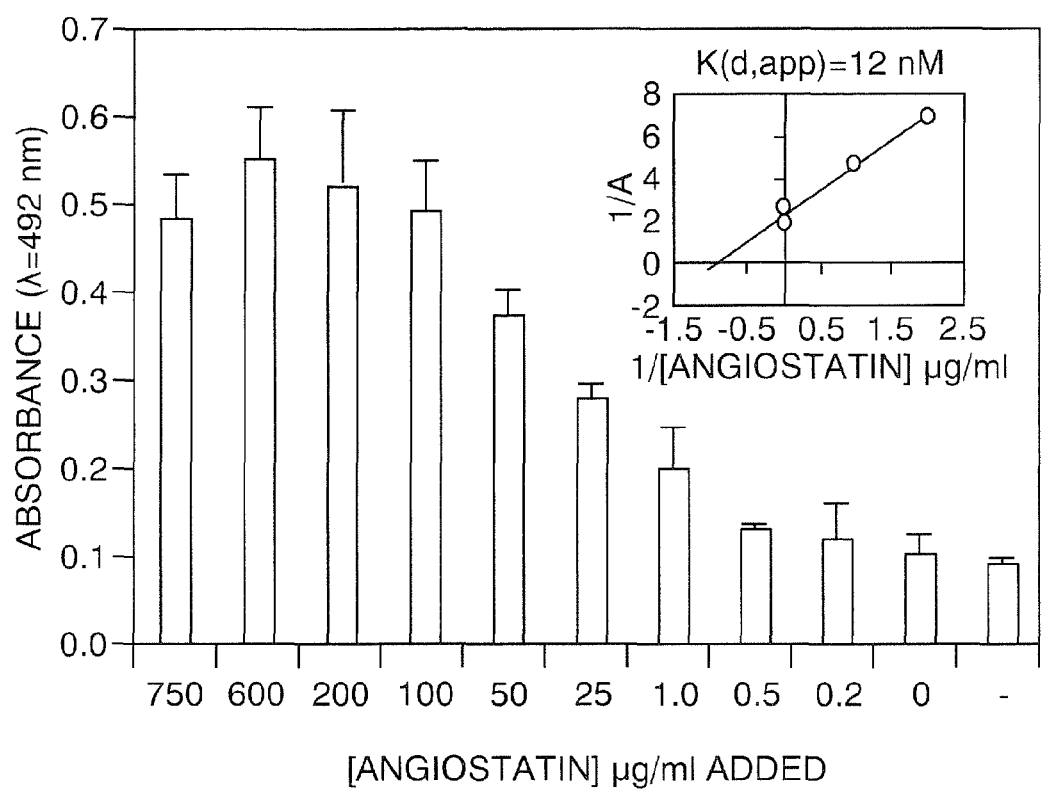

FIG. 11 is a bar graph showing the binding of angiostatin to purified bovine $F_1$ ATP synthase. ELISA was used to determine concentration-dependent binding of angiostatin to a constant amount of $F_1$ ATP synthase. Each well was coated with 1 μg of $F_1$ ATP synthase prior to addition of decreasing amounts of angiostatin. Control lane (-) shows binding of secondary antibody only. n=6 Inset, Apparent dissociation constants ($K_{d(app)}$) were determined from double-reciprocal plots of the binding data. Angiostatin bound to bovine $F_1$ ATP synthase with a $K_{d(app)}$ of 12 nM.

Figure 12:
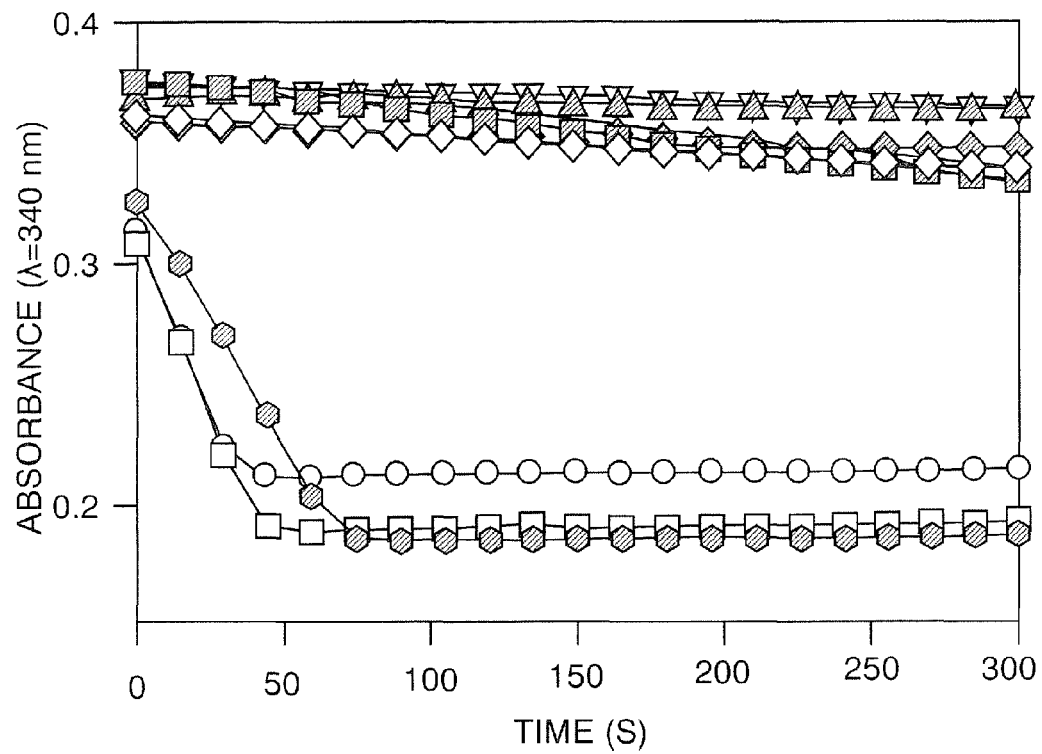

FIG. 12 is a bar graph showing the inhibition of purified $F_1$ ATP synthase by angiostatin. Purified $F_1$ ATP synthase activity was measured spectrophotometrically at λ=340 nm by coupling the production of ADP to the oxidation of NADH via the pyruvate kinase and lactate dehydrogenase reaction in which a decrease in the absorbance at λ=340 nm indicates active protein (dark six membered rings). Angiostatin (10 M) completely inhibited purified $F_1$ ATP synthase activity (light six membered rings), comparable to a known $F_1$ ATP synthase inhibitor, $NaN_3$ (2%) (dark diamonds) and an enzyme free control (dark triangles). Polyclonal antibodies directed against the recombinant alpha-subunit of ATP synthase (500 g/ml) (inverted dark triangles) and beta-subunit ATP synthase (700 g/ml) (inverted light triangles) abolished ATPase activity. A monoclonal antibody to the alpha-subunit of ATP synthase (25 g/ml) also inhibited activity (dark squares). Control antibodies had no effect on activity (light circles and squares). Representative data shown, n=3.

Figure 13:
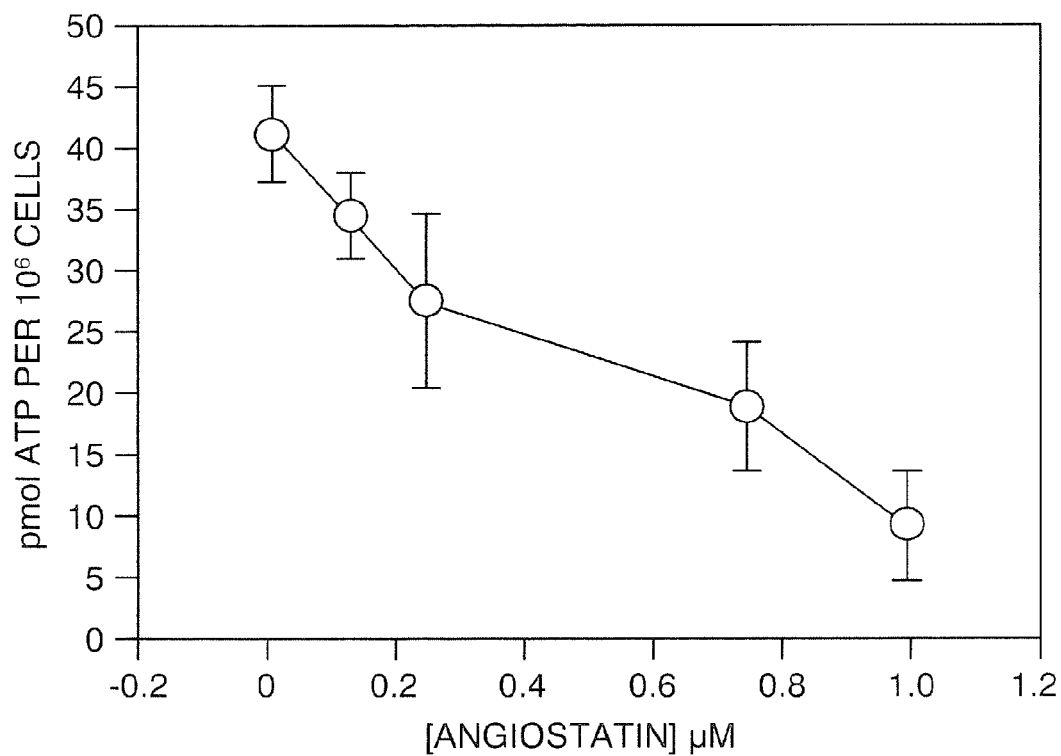

FIG. 13 is a bar graph showing the inhibition of ATP generation by angiostatin on the surface of HUVEC as measured by bioluminescent luciferase assay. ATP generation on the surface of HUVEC was inhibited in a dose-dependent manner in the presence of increasing concentrations of angiostatin. Representative data shown, n=3.

DETAILED DESCRIPTION OF THE INVENTION

The following description includes the best presently contemplated mode of carrying out the invention. This description is made for the purpose of illustrating the general principles of the inventions and should not be taken in a limiting sense.

Compounds, compositions and methods for promoting or inhibiting angiogenesis are disclosed. Also disclosed are screening methods for identifying compounds that bind to the alpha and/or beta subunits of F1 ATP synthase in a manner that inhibits angiostatin binding as well as compounds that bind in an allosteric position. Methods for determining whether such compounds function as agonists, antagonists, partial agonists, inverse agonists, allosteric promoters or allosteric inhibitors are also disclosed.

The present invention is based on the discovery that angiostatin binds to both the alpha and beta subunits of F1 ATP synthase and, through this binding, inhibits angiogenesis. The active site on ATP synthase that shuts down ATP synthesis is small and embedded in the beta subunit. While not wishing to be bound to a particular theory, it is believed that only small molecules will actually fit into that site, so it is not likely that angiostatin, with a molecular weight of about 35,000, or other large molecules that have molecular weights in excess of about 2000, such as antibodies to the alpha and/or beta subunits of F1 ATP synthase, with molecular weights of about 150,000, actually bind in that site. Accordingly, it is believed that the effect of angiostatin and other large molecules is likely a steric effect.

Compounds that bind to the alpha and/or beta subunits of F1 ATP synthase can inhibit the ability of angiostatin to bind to these subunits, and, accordingly, inhibit the ability of angiostatin to inhibit angiogenesis. However, the compounds, once bound, may themselves function as angiogenesis inhibitors, and mimic the function of angiostatin. The compounds might also function as partial agonists, inverse agonists, or antagonists.

Other compounds do not inhibit the ability of angiostatin to bind to F1 ATP synthase, but have an effect on the ability of angiostatin, angiostatin agonists or angiostatin partial agonists, once bound, to inhibit angiogenesis. Such compounds are referred to herein as allosteric modulators, and, depending on their effect, as allosteric promoters or allosteric inhibitors.

Definitions

The following definitions will be helpful in understanding the compositions and methods described herein.

As used herein, the term "angiogenesis" is defined as the generation of new blood vessels into a tissue or organ. The term "endothelium" means a thin layer of flat epithelial cells that lines serous cavities, lymph vessels, and blood vessels.

As used herein, the term "$F_1$-$F_O$ ATP Synthase holoenzyme" (also referred to herein as "ATP synthase") is a multi-subunit enzyme that functions in ATP metabolism and is typically found in the matrix of all mitochondria. ATP synthase couples proton flux across a membrane to the metabolism of ATP. There are two major complexes that together constitute the holoenzyme. The $F_1$ complex contains multiple subunits ($α_3β_3γδε$) and acts as the catalytic site for ATP synthesis, whereas the membrane-embedded $F_O$ complex (multiple subunits each of a, b, and c) forms a proton channel and structural attachment for $F_1$ (Penefsky and Cross, (1991). Structure and mechanism of $FoF_1$-type ATP synthases and ATPases. *Adv Enzymol Relat Areas Mol Biol* 64, 173-214). The $F_O$ complex typically forms a proton channel through the inner mitochondrial membrane, but also forms a channel through the plasma membrane in certain cells such as endothelial cells. Passage of protons through a channel formed by the a subunits causes the ring formed by the c subunits to rotate. The catalytic $F_1$ complex is attached to $F_O$ and faces into the mitochondrial matrix, or into the extracellular milieu in the case of endothelial cells. Rotation of the $F_O$ c-ring is coupled to rotation of the $F_1$ γ-subunit. The other end of the γ-subunit resides within a ring formed by three α and three β subunits arranged as a trimer of α-βdimers. The β-subunits perform a structural function whereas the β-subunits are catalytic in ATP synthesis and hydrolysis. As the γ-subunit rotates, it induces a series of conformational changes in the β-subunits caused by asymmetric protein-protein interactions between the γ-subunit and each of the three β-subunits. The three β-subunits are believed to proceed sequentially through conformational changes that facilitate the binding of ADP, phosphorylation to ATP, and release of the nascent ATP molecule (Boyer, (1997) The ATP synthase-a splendid molecular machine. *Ann Rev Biochem* 66, 717-49).

The term "angiostatin" refers to a proteolytic fragment of plasminogen, and includes at least one, and preferably, at least three kringles from plasminogen. Angiostatin is a potent inhibitor of angiogenesis and the growth of tumor cell metastases (O'Reilly et al., Cell 79:315-328 (1994)). All anti-angiogenic forms of angiostatin are intended to be included within the definition of angiostatin as used herein.

Angiostatin has a specific three dimensional conformation that is defined by the kringle region of the plasminogen molecule. (Robbins, K. C., "The plasminogen-plasmin enzyme system" Hemostasis and Thrombosis, Basic Principles and Practice, 2nd Edition, ed. by Colman, R. W. et al. J. B. Lippincott Company, pp. 340-357, 1987). There are five such kringle regions, which are conformationally related motifs and have substantial sequence homology in the amino terminal portion of the plasminogen molecule.

A variety of silent amino acid substitutions, additions, or deletions can be made in the above identified kringle fragments, which do not significantly alter the fragments' endothelial cell inhibiting activity. Each kringle region of the angiostatin molecule contains approximately 80 amino acids and contains 3 disulfide bonds. Anti-angiogenic angiostatin can include a varying amount of amino- or carboxy-terminal amino acids from the inter-kringle regions and may have some or all of the naturally occurring di-sulfide bonds reduced. Angiostatin may also be provided in an aggregate, non-refolded, recombinant form.

Angiostatin can be generated in vitro by limited proteolysis of plasminogen, as taught by Sottrup-Jensen et al., *Progress in Chemical Fibrinolysis and Thrombolysis* 3:191-209 (1978), the contents of which are hereby incorporated by reference for all purposes. This results in a 38 kDa plasminogen fragment (Va179-Pro353). Angiostatin can also be generated in vitro by reducing plasmin (Gately et al. PNAS 94:10868-10872 (1997)) and in Chinese hamster ovary and human fibrosarcoma cells (Stathakis et al., JBC 272(33): 20641-20645 (1997)).

Angiostatin may also be produced from recombinant sources, from genetically altered cells implanted into animals, from tumors, and from cell cultures as well as other sources. Angiostatin can be isolated from body fluids including, but not limited to, serum and urine. Recombinant techniques include gene amplification from DNA sources using the polymerase chain reaction (PCR), and gene amplification from RNA sources using reverse transcriptase/PCR.

The term "angiostatin agonist" as used herein refers to a compound (other than angiostatin) that inhibits binding of angiostatin to the alpha and/or beta subunits of F1 ATP synthase, and that binds to the alpha and/or beta subunits of F1 ATP synthase. When so bound, the compound inhibits angiogenesis to a level equal to or greater than angiostatin itself.

The term "angiostatin partial agonist" as used herein refers to a compound that inhibits binding of angiostatin to the alpha and/or beta subunits of F1 ATP synthase, and that binds to the alpha and/or beta subunits of F1 ATP synthase. When so bound, the compound inhibits angiogenesis, but to a level less than angiostatin itself.

The term "angiostatin antagonist" as used herein refers to a compound that inhibits binding of angiostatin to the alpha and/or beta subunits of F1 ATP synthase, and that binds to the alpha and/or beta subunits of F1 ATP synthase. When so bound, the compound promotes angiogenesis or, at a minimum, has little or no effect on angiogenesis, thus promoting angiogenesis by inhibiting the ability of angiostatin to inhibit angiogenesis.

The term "angiostatin allosteric promoter" as used herein refers to a compound that does not inhibit the binding of angiostatin to the alpha and/or beta subunits of F1 ATP synthase, but that binds to the alpha and/or beta subunits of F1 ATP synthase in a different position on these subunits. When so bound, the compound promotes the ability of angiostatin or other angiostatin agonists or partial agonists to inhibit angiogenesis.

The term "angiostatin allosteric inhibitor" as used herein refers to a compound that does not inhibit the binding of angiostatin to the alpha and/or beta subunits of F1 ATP synthase, but that binds to the alpha and/or beta subunits of F1 ATP synthase in a different position on these subunits. When so bound, the compound inhibits the ability of angiostatin or other angiostatin agonists or partial agonists to inhibit angiogenesis.

The term "angiostatin allosteric modulator" as used herein refers to angiostatin allosteric promoters and inhibitors.

The terms "a", "an" and "the" as used herein are defined to mean "one or more" and include the plural unless the context is inappropriate.

As employed herein, the phrase "active agent" or "active compound" refers to angiostatin agonists, antagonists, partial agonists, inverse agonists or allosteric modulators. Examples of suitable biologically active compounds/agents include antibodies, antibody fragments, enzymes, peptides, nucleic acids, and small molecules.

As used herein, peptide is defined as including less than or equal to 100 amino acids and protein is defined as including 100 or more amino acids.

Unless defined otherwise, all technical and scientific terms used herein have the same meaning as commonly understood by one having ordinary skill in the art. Although other materials and methods similar or equivalent to those described herein can be used in the practice or testing of the present invention, as would be apparent to practitioners in the art, the preferred methods and materials are now described.

Although the alpha and beta subunits of F1 ATP synthase are described as the binding site for angiostatin, ATP synthase couples proton flux across a membrane to rotation of the gamma subunit, which in turn induces cyclical conformational changes in the catalytic beta subunit. Compounds that inhibit the rotation of the gamma subunit would also be expected to modulate angiogenesis.

I. Methods of Inhibiting Angiogenesis

There are several methods for inhibiting angiogenesis. Angiogenesis can be inhibited by administering an effective amount of a suitable angiostatin agonist or partial agonist (for example, antibodies, antibody fragments, and/or small molecules) to a patient in need of such treatment. Angiostatin allosteric promoters can also be administered, alone or in combination with the angiostatin agonists and/or partial agonists. The compounds can either inhibit angiogenesis on their own, or allosterically enhance the ability of angiostatin (or other antagonists of F1 ATP synthase) to inhibit angiogenesis. The methods can be used to treat tumors, various autoimmune disorders, hereditary disorders, ocular disorders and other angiogenesis-mediated disorders.

The therapeutic and diagnostic methods described herein typically involve administering an effective amount of the compositions described herein to a patient. The exact dose to be administered will vary according to the use of the compositions and on the age, sex and condition of the patient, and can readily be determined by the treating physician. The compositions may be administered as a single dose or in a continuous manner over a period of time. Doses may be repeated as appropriate.

The compositions and methods can be used to treat angiogenesis-mediated disorders including hemangioma, solid tumors, leukemia, metastasis, telangiectasia, psoriasis, scleroderma, pyogenic granuloma, myocardial angiogenesis, Crohn's disease, plaque neovascularization, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, *Helicobacter* related diseases, fractures, keloids, and vasculogenesis. Specific disorders that can be treated, and compounds and compositions useful in these methods, are described in more detail below.

A. Carcinomas/Tumors

Carcinomas that can be treated using the compounds, compositions and methods described herein include colorectal carcinoma, gastric carcinoma, signet ring type, esophageal carcinoma, intestinal type, mucinous type, pancreatic carcinoma, lung carcinoma, breast carcinoma, renal carcinoma, bladder carcinoma, prostate carcinoma, testicular carcinoma, ovarian carcinoma, endometrial carcinoma, thyroid carcinoma, liver carcinoma, larynx carcinoma, mesothelioma, neuroendocrine carcinomas, neuroectodermal tumors, melanoma, gliomas, neuroblastomas, sarcomas, leiomyosarcoma, MFII, fibrosarcoma, liposarcoma, MPNT, chondrosarcoma, and lymphomas.

B. Ocular Disorders Mediated by Angiogenesis

Various ocular disorders are mediated by angiogenesis, and can be treated using the compounds, compositions and methods described herein. One example of a disease mediated by angiogenesis is ocular neovascular disease, which is characterized by invasion of new blood vessels into the structures of the eye and is the most common cause of blindness. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis. Vitamin A deficiency, atopic keratitis, superior limbic keratitis, pterygium keratitis sicca, periphigoid radial keratotomy, and corneal graph rejection.

Diseases associated with retinal/choroidal neovascularization include, but are not limited to, diabetic retinopathy, macular degeneration, presumed myopia, optic pits, chronic retinal detachment, hyperviscosity syndromes, trauma and post-laser complications. Other diseases include, but are not limited to, diseases associated with rubeosis (neovascularization of the angle) and diseases caused by the abnormal proliferation of fibrovascular or fibrous tissue including all forms of proliferative vitreoretinopathy.

C. Inflammation

The methods described herein can also be used to treat angiogenesis-mediated disorders such as various forms of arthritis, including rheumatoid arthritis. In these methods, treatment with combinations of the compounds described herein with other agents useful for treating the disorders, such as cyclooxygenase-2 (COX-2) inhibitors, which are well known to those of skill in the art.

The blood vessels in the synovial lining of the joints can undergo angiogenesis. The endothelial cells form new vascular networks and release factors and reactive oxygen species that lead to pannus growth and cartilage destruction. These factors are believed to actively contribute to rheumatoid arthritis and also to osteoarthritis. Chondrocyte activation by angiogenic-related factors contributes to joint destruction, and also promotes new bone formation. The methods described herein can be used as a therapeutic intervention to prevent bone destruction and new bone formation.

Pathological angiogenesis is also believed to be involved with chronic inflammation. Examples of disorders that can be treated using the compounds, compositions and methods described herein include ulcerative colitis, Crohn's disease, bartonellosis, and atherosclerosis.

II. Methods of Promoting Angiogenesis

It is often desirable to promote angiogenesis, particularly to assist in wound healing, or to provide vascularization to occluded vessels or organs or tissue where insufficient vascularization exists. Compounds that promote angiogenesis can be used to treat conditions of vascular insufficiency, including ischemic heart disease, peripheral vascular disease, thromboembolic disease, stroke and vasculititis (Buerger's disease, Wegener's granulomatosis, and Giant Cell Arteritis). Such compounds can also be used at wound sites to promote healing, and at sites of transplantation and grafting (e.g., skin grafting). Spinal cord injuries can also be expected to benefit from intervention of vascularization.

There are several methods for promoting angiogenesis. On the cellular level, angiogenesis can be promoted by binding a suitable compound (for example, antibodies, antibody fragments and/or small molecules) to the alpha or beta subunit of F1 ATP synthase in a manner that inhibits the ability of angiostatin to bind to the subunits, provided that the compound itself does not itself inhibit angiogenesis when bound to the subunits. Some compounds do not directly inhibit angiogenesis, but block the ability of angiostatin to inhibit angiogenesis, indirectly promoting angiogenesis. Other compounds directly promote angiogenesis by promoting ATP synthesis. These types of compounds are referred to herein as angiostatin antagonists. Angiostatin allosteric inhibitors can also be used.

The methods involve administering to a patient in need of treatment thereof an effective, angiogenesis promoting amount of an angiostatin antagonist and/or angiostatin allosteric inhibitor. An effective, angiogenesis promoting amount of such compounds is defined herein as an amount sufficient to promote angiogenesis in a patient. The amount of such compounds, and the duration of treatment, can be readily determined by a treating physician, for example, by monitoring blood flow or other signs of increased vascularization at a desired location in a patient.

Compounds and compositions useful in the angiogenesis inhibiting and angiogenesis promoting methods are described in more detail below.

III. Compounds for Promoting or Inhibiting Angiogenesis

Various compounds, including various antibodies, can bind to a position on the alpha or beta subunits of F1 ATP synthase and inhibit angiostatin binding. However, the mere fact that they inhibit angiostatin binding does not determine their ultimate effect on angiogenesis. Such compounds can act as angiostatin agonists, partial agonists, inverse agonists or antagonists.

Various compounds, including various antibodies, bind to an allosteric position on the alpha and/or beta subunits of F1 ATP synthase and exercise their effect on angiostatin (or angiostatin agonists, partial agonists, inverse agonists or antagonists) in an allosteric manner, as allosteric promoters or inhibitors. The mere fact that the compounds bind to the alpha or beta subunits in a position that does not significantly interfere with angiostatin binding does not determine their ultimate effect on the ability of angiostatin (or an agonist, partial agonist, inverse agonist or antagonist as described above) to effect angiogenesis.

The activity of the compounds once bound can be readily determined using the assays described herein. The compounds described herein are not limited to a particular molecular weight. In some cases, large compounds such as antibodies can be preferred since their effect is mostly; steric, and therefore will not likely inhibit the function of ATP synthase systemically, only in vascular endothelial cells. In other cases, small molecules may be easier to produce in commercial quantities and may be provided in relatively larger doses. The compounds can be large molecules (i.e., those with a molecular weight above about 1000) or small molecules (i.e., those with a molecular weight below about 1000). Examples of suitable types of compounds include antibodies, antibody fragments, enzymes, peptides and oligonucleotides.

A. Antibodies

Antibodies can be generated that bind to the alpha and/or beta subunits of F1 ATP synthase. Polyclonal antibodies can be used, provided their overall effect is a desired effect (i.e., an angiogenic or an anti-angiogenic effect, as desired). However, monoclonal antibodies are preferred. Humanized (chimeric) antibodies can be even more preferred.

Angiostatin primarily binds to the outside surface of the alpha and/or beta subunits of F1 ATP synthase, not to the inside of the subunits. The antibodies may not and need not bind in exactly the same way as angiostatin. Angiostatin has several potential binding portions (possibly involving the various kringles), and the antibodies likely do not include portions that mimic each of these binding portions. However, the antibodies may inhibit angiostatin binding by sterically interfering with and/or binding to all or part of the actual angiostatin binding site(s).

Antibodies, in particular, monoclonal antibodies (mAbs) have been developed against the alpha and/or beta subunits of F1 ATP synthase that can be used either to directly inhibit angiogenesis or to target cytotoxic drugs or radioisotopic or other labels to sites of angiogenesis. Because angiogenesis does not occur to a large extent in adults, except following tissue injury, the antibodies can be extremely specific. Furthermore, unlike other lines of research which have produced cancer cell-specific mAbs to target cytotoxic drugs to tumors, these mAbs are prepared against host antigens (i.e., the alpha and beta subunits of F1 ATP synthase). This approach has the major advantage that generation of "resistant" variants of the tumor cannot occur and, in theory, one mAb can be used to treat all solid tumors. An additional advantage is that endothelial cells, by virtue of their vascular location, are very accessible to antibodies in the circulation.

Antibody Preparation

The term "antibody" refers to a polypeptide substantially encoded by an immunoglobulin gene or immunoglobulin genes, or fragments thereof, that specifically binds and recognizes an analyte (antigen, in this case the alpha and/or beta subunits of F1 ATP synthase, preferably human F1 ATP synthase). Immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit includes a tetramer. Each tetramer is composed of two identical pairs of polypeptide chains, each pair having one "light" (about 25 kD) and one "heavy" chain (about 50-70 kD). The N-terminus of each chain has a variable region of about 100 to 110 or more amino acids primarily responsible for antigen recognition. The terms "variable light chain" (or "VL") and "variable heavy chain" (or "VH") refer to these light and heavy chains, respectively.

Antibodies exist, for example, as intact immunoglobulins or as a number of well characterized antigen-binding fragments produced by digestion with various peptidases. For example, pepsin digests an antibody below the disulfide linkages in the hinge region to produce an F(ab')$_2$ fragment, a dimer of Fab which itself is a light chain joined to VH-CH1 by a disulfide bond. The F(ab')$_2$ fragment can be reduced under mild conditions to break the disulfide linkage in the hinge region, thereby converting the F(ab')$_2$ dimer into an Fab' monomer. The Fab' monomer is essentially an Fab with part of the hinge region (see *Fundamental Immunology*, Third Edition, W. E. Paul (ed.), Raven-Press, N.Y. (1993), the contents of which are hereby incorporated by reference). While various antibody fragments are defined in terms of the digestion of an intact antibody, one of ordinary skill in the art will appreciate that such fragments can be synthesized de novo either chemically or by using recombinant DNA methodology. Thus, the term antibody, as used herein, also includes antibody fragments, such as a single chain antibody, an antigen binding F(ab')2 fragment, an antigen binding Fab' fragment, an antigen binding Fab fragment, an antigen binding Fv fragments a single heavy chain or a chimeric (humanized) antibody. Such antibodies can be produced by modifying whole antibodies or synthesized de novo using recombinant DNA methodologies.

The alpha and/or beta subunits of F1 ATP synthase (including fragments, derivatives, and analogs thereof) can be used as an immunogen to generate antibodies which immunospecifically bind such immunogens. Such antibodies include but are not limited to polyclonal antibodies, monoclonal antibodies, chimeric antibodies, single chain antibodies, antigen binding antibody fragments (e.g., Fab, Fab', F(ab')$_2$, Fv, or hypervariable regions), and mAb or Fab expression libraries. In some embodiments, polyclonal and/or monoclonal antibodies to the alpha and/or beta subunits of F1 ATP synthase are produced. In yet other embodiments, fragments of the alpha and/or beta subunits of F1 ATP synthase that are identified as immunogenic are used as immunogens for antibody production.

Various procedures known in the art can be used to produce polyclonal antibodies. Various host animals (including, but not limited to, rabbits, mice, rats, sheep, goats, camels, and the like) can be immunized by injection with the antigen, fragment, derivative or analog. Various adjuvants can be used to increase the immunological response, depending on the host species. Such adjuvants include, for example, Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and other adjuvants, such as BCG (bacille Calmette-Guerin) and *Corynebacterium parvum*.

Any technique that provides for the production of antibody molecules by continuous cell lines in culture can be used to prepare monoclonal antibodies directed toward the alpha and/or beta subunits of F1 ATP synthase. Such techniques include, for example, the hybridoma technique originally developed by Kohler and Milstein (se, e.g., *Nature* 256:495-97 (1975)), the trioma technique (e, e.g., Hagiwara and Yuasa, *Hum. Antibodies Hybridomas* 4:15-19 (1993); Hering et al., *Biomed. Biochim. Acta* 47:211-16 (1988)), the human B-cell hybridoma technique (se, e.g., Kozbor et al., *Immunology Today* 4:72 (1983)), and the EBV-hybridoma technique to produce human monoclonal antibodies (se, e.g., Cole et al., In: *Monoclonal Antibodies and Cancer Therapy*, Alan R. Liss, Inc., pp. 77-96 (1985)). Human antibodies can be used and can be obtained by using human hybridomas (see, e.g., Cote et al., *Proc. Natl. Acad. Sci. USA* 80:2096-30 (1983)) or by transforming human B cells with EBV virus in vitro (see, e.g., Cole et al., supra).

"Chimeric" or "humanized" antibodies (see, e.g., Morrison et al., *Proc. Natl. Acad. Sci. USA* 81:6851-55 (1984); Neuberger et al., *Nature* 312:604-08 (1984); Takeda et al., *Nature* 314:452-54 (1985)) can also be prepared. Such chimeric antibodies are typically prepared by splicing the non-human genes for an antibody molecule specific for antigen together with genes from a human antibody molecule of appropriate biological activity. It can be desirable to transfer the antigen binding regions (e.g., Fab', F(ab')$_2$, Fab, Fv, or hypervariable regions) of non-human antibodies into the framework of a human antibody by recombinant DNA techniques to produce a substantially human molecule. Methods for producing such "chimeric" molecules are generally well known and described in, for example, U.S. Pat. Nos. 4,816,567; 4,816,397; 5,693,762; and 5,712,120; PCT Patent Publications WO 87/02671 and WO 90/00616; and European Patent Publication EP 239 400 (the disclosures of which are incorporated by reference herein). Alternatively, a human monoclonal antibody or portions thereof can be identified by first screening a cDNA library for nucleic acid molecules that encode antibodies that specifically bind to the alpha and/or beta subunits of F1 ATP synthase according to the method generally set forth by Huse et al. (*Science* 246:1275-81 (1989)), the contents of which are hereby incorporated by reference. The nucleic acid molecule can then be cloned and amplified to obtain sequences that encode the antibody (or antigen-binding domain) of the desired specificity. Phage display technology offers another technique for selecting antibodies that bind to the alpha and/or beta subunits of F1 ATP synthase, fragments, derivatives or analogs thereof. (See, e.g., International Patent Publications WO 91/17271 and WO 92/01047; Huse et al., supra.)

Techniques for producing single chain antibodies (see, e.g., U.S. Pat. Nos. 4,946,778 and 5,969,108) can also be used. An additional aspect of the invention utilizes the techniques described for the construction of a Fab expression library (see, e.g., Huse et al., supra) to allow rapid and easy identification of monoclonal Fab fragments with the desired specificity for antigens, fragments, derivatives, or analogs thereof.

Antibodies that contain the idiotype of the molecule can be generated by known techniques. For example, such fragments include but are not limited to, the F(ab'), fragment which can be produced by pepsin digestion of the antibody molecule, the Fab' fragments which can be generated by reducing the disulfide bridges of the F(ab')$_2$ fragment, the Fab fragments which can be generated by treating the antibody molecule with papain and a reducing agent, and Fv fragments. Recombinant Fv fragments can also be produced in eukaryotic cells using, for example, the methods described in U.S. Pat. No. 5,965,405 (the disclosure of which is incorporated by reference herein).

Antibody screening can be accomplished by techniques known in the art (e.g., ELISA (enzyme-linked immunosorbent assay)). In one example, antibodies that recognize a specific domain of an antigen can be used to assay generated hybridomas for a product which binds to polypeptides containing that domain. Antibodies specific to a domain of an antigen are also provided.

Antibodies against the alpha and/or beta subunits of F1 ATP synthase (including fragments, derivatives and analogs) can be used for passive antibody treatment, according to methods known in the art. The antibodies can be produced as described above and can be polyclonal or monoclonal antibodies and administered intravenously, enterally (e.g., as an enteric coated tablet form), by aerosol, orally, transdermally, transmucosally, intrapleurally, intrathecally, or by other suitable routes.

Small amounts of humanized antibody can be produced in a transient expression system in CHO cells to establish that they bind to HUVEC cells expressing F1 ATP synthase. Stable cell lines can then be isolated to produce larger quantities of purified material.

The binding affinity of murine and humanized antibodies can be determined using the procedure described by Krause et al., *Behring Inst. Mitt.*, 87:56-67 (1990). Briefly, antibodies can be labeled with fluorescein using fluorescein isothiocyanate (FITC), and then incubated with HUVEC cells for two hours on ice in PBS containing fetal calf serum (FCS) and sodium azide. The amount of fluorescence bound per cell can be determined in a FACScan and calibrated using standard beads. The number of molecules of antibody that had bound per cell at each antibody concentration can be established and used to generate Scatchard plots. Competition assays can be performed by FACScan quantitation of bound antibody after incubating the cells with a standard quantity of the murine antibody together with a dilution series of the humanized variants.

Multivalent Compounds

Multivalent compounds are defined herein as compounds that include more than one moiety capable of being attached to the alpha, beta, delta, gamma and, or epsilon subunits of F1 ATP synthase, the a, b or c subunits on $F_O$ ATP synthase and/or one or more allosteric positions on the F1/F0 ATP synthase (either on the subunits themselves or a junctional positions at the interface between the subunits). Preferably, at least one moiety binds to the alpha and/or beta subunits of F1 ATP synthase or an allosteric position on the F1 ATP synthase.

In one embodiment, the multifunctional compound includes at least one protein and/or peptide chain. Alternatively, the compound can include small molecules with a plurality of moieties with bind properties as described above.

High Throughput Screening Methods for mAb Libraries

High throughput monoclonal antibody assays can be used to determine the binding affinities of the antibodies to the subunits, and also identify which antibodies act as agonists, partial agonists, inverse agonists, antagonists and allosteric modulators of F1 ATP synthase, in particular, to the alpha and/or beta subunits thereof. The assays can evaluate, for example, increased or decreased ATP levels or the degree of cellular proliferation. Suitable assays are described, for example, in the Examples. Similar high throughput assays can be used to evaluate the properties of small molecule libraries.

Similar screening methods can be used to identify other classes of compounds useful in the methods described herein. Combinatorial libraries of compounds, for example, phage display peptide libraries, small molecule libraries and oligonucleotide libraries can be screened. Compounds that bind to the alpha and/or beta subunits of F1 ATP synthase can be identified, for example, using competitive binding studies. The effect of the compounds once bound to the F1 ATP synthase can be determined, for example, by evaluating the level of ATP synthesis, the proliferation of human vascular endothelial cells (HUVEC) and/or the viability and/or growth of tumors.

Antibody/Drug Conjugates

Antibodies raised against the alpha and/or beta subunits of ATP synthase, and, in particular, monoclonal antibodies, can be conjugated to a drug. The drug/antibody complex can then be administered to a patient, and the antibody will bind to the ATP synthase in a manner that delivers a relatively high concentration of the drug to the desired tissue or organ. In some embodiments, the binding of the drug to the antibody is in a biodegradable linkage, so that the drug is released over time. In other embodiments, the drug remains attached to the antibody.

Anti-cancer drugs are an example of drugs that can be conjugated to the antibodies. For example, the antibodies can be conjugated with QFA, which is an antifolate, or with calicheamycin, adriaicin, bleomycin or vincamycin, which are anti-tumor antibiotics that cleave the double-stranded DNA of tumor cells. Additional tumor-treating compounds that can be coupled to the antibodies include BCNU, streptozoicin, vincristine, ricin, radioisotopes, and 5-fluorouracil and other anti-cancer nucleosides.

In vivo xenograft studies can be used to show that tumor inhibition with limited normal tissue damage can be obtained with antibodies conjugated to these anti-cancer drugs. The antibody/drug conjugates can be used to target compounds directly to tumors that might otherwise be too toxic when administered systemically.

The conjugates are most advantageously used in combination with targeted drug delivery methods, for example, by placing the compounds in liposomes or other microparticles of an appropriate size such that they lodge in capillary beds around tumors and release the compounds at the tumor site. Alternatively the compounds can be injected directly into or around the site of a tumor, for example, via injection or catheter delivery. Such methods minimize any undesirable systemic effects.

Oligonucleotides with free, reactive hydroxy, amine, carboxy or thiol groups at either the 3' or 5' end can be conjugated to free reactive groups on antibodies using conventional coupling chemistry, for example, using heterobifunctional reagents such as SPDP. The 3' or 5' end of the oligonucleotide can be enzymatically labeled, for example, with $^{32}P$ as tracer for DNA. The final product can be tested for cell-binding activity and protein and bound oligonucleotide concentrations. Depending on the activity of the oligonucleotides, the conjugates can be used for therapeutic or diagnostic purposes.

The antibodies (or other compounds that bind to the alpha and/or beta subunits of F1 ATP synthase) can be conjugated with photosensitizers such as porphyrins and used in targeted photodynamic therapy. After the compositions are administered and allowed to bind to the F1 ATP synthase in vascular cells, the photodynamic therapy can be conducted by irradiation with light at a suitable wavelength for a suitable amount of time.

Antibodies that bind to the alpha and/or beta subunits of F1 ATP synthase can also be covalently or ionically coupled to various markers, and used to detect the presence of tumors. This generally involves administering a suitable amount of the antibody to the patient, waiting for the antibody to bind to the F1 ATP synthase at or around a tumor site, and detecting the marker. Suitable markers are well known to those of skill in the art, and include for example, radioisotopic labels, fluorescent labels and the like, and detection methods for these markers are also well known to those of skill in the art. Examples of suitable detection techniques include positron emission tomography, autoradiography, flow cytometry, radioreceptor binding assays, and immunohistochemistry.

Generally, a background concentration of the compounds will be observed in locations throughout the body. However, a higher, detectable concentration will be observed in locations where a tumor is present. The label can be detected, and, accordingly, the tumors can be detected.

B. Small Molecules

As used herein, small molecules are defined as molecules with molecular weights below about 2000, except in the case of oligonucleotides that can be considered small molecules if their molecular weight is less than about 10,000 (about 30 mer or less). Many companies currently generate libraries of small molecules, and high throughput screening methods for evaluating small molecule libraries to identify compounds that bind particular receptors are well known to those of skill in the art. Combinatorial libraries of small molecules can be screened and suitable compounds for use in the methods described herein can be identified using routine experimentation. One example of a suitable small molecule library is a phage display library. Another such library is a library including random oligonucleotides, typically with sizes less than about 100 mers. The SELEX process can be used to screen such oligonucleotide libraries (including DNA, RNA and other types of genetic material, and also including natural and non-natural base pairs) for compounds that have suitable binding properties, and other assays can be used to determine the effect of the compounds on angiogenesis.

The SELEX method is described in U.S. Pat. No. 5,270,163 to Gold et al. Briefly, a candidate mixture of single stranded nucleic acids with regions of randomized sequence can be contacted with the alpha and/or beta subunits of F1 ATP synthase and those nucleic acids having an increased affinity to the subunits can be partitioned from the remainder of the candidate mixture. The partitioned nucleic acids can be amplified to yield a ligand enriched mixture.

C. Peptide Phage Display Libraries

One technique that is useful for identifying peptides that bind to F1 ATP synthase or the alpha and/or beta subunits thereof is phage-display technology, as described, for example, in Phage Display of Peptides and Proteins: A Laboratory Manual; Edited by Brian K. Kay et al. Academic Press San Diego, 1996, the contents of which are hereby incorporated by reference for all purposes.

Phage peptide libraries typically include numerous different phage clones, each expressing a different peptide, encoded in a single-stranded DNA genome as an insert in one of the coat proteins. In an ideal phage library the number of individual clones would be $20^n$, where "n" equals the number of residues that make up the random peptides encoded by the phage. For example, if a phage library was screened for a seven residue peptide, the library in theory would contain $20^7$ (or $1.28 \times 10^9$) possible 7-residue sequences. Therefore, a 7-mer peptide library should contain approximately $10^9$ individual phage.

Methods for preparing libraries containing diverse populations of various types of molecules such as antibodies, peptides, polypeptides, proteins, and fragments thereof are known in the art and are commercially available (see, for example, Ecker and Crooke, *Biotechnology* 13:351-360 (1995), and the references cited therein, the contents of each of which is incorporated herein by reference for all purposes). One example of a suitable phage display library is the Ph.D.-7 phage display library (New England BioLabs Cat #8100), a combinatorial library consisting of random peptide 7-mers. The Ph.D.-7 phage display library consists of linear 7-mer peptides fused to the pIII coat protein of M13 via a Gly-Gly-Gly-Ser flexible linker. The library contains $2.8 \times 10^9$ independent clones and is useful for identifying targets requiring binding elements concentrated in a short stretch of amino acids.

Phage clones displaying peptides that are able to bind to F1 ATP synthase or subunits thereof are selected from the library. The sequences of the inserted peptides are deduced from the DNA sequences of the phage clones. This approach is particularly desirable because no prior knowledge of the primary sequence of the target protein is necessary, epitopes represented within the target, either by a linear sequence of amino acids (linear epitope) or by the spatial juxtaposition of amino acids distant from each other within the primary sequence (conformational epitope) are both identifiable, and peptidic mimotopes of epitopes derived from non-proteinaceous molecules such as lipids and carbohydrate moieties can also be generated.

A library of phage displaying potential binding peptides can be incubated with immobilized F1 ATP synthase, or the alpha and/or beta subunits thereof, to select clones encoding recombinant peptides that specifically bind the immobilized ATP synthase or subunits thereof. The phages can be amplified after various rounds of biopanning (binding to the immobilized F1 ATP synthase or alpha and/or beta subunits thereof) and individual viral plaques, each expressing a different recombinant protein, or binding peptide, can then be expanded to produce sufficient amounts of peptides to perform a binding assay.

Phage selection can be conducted according to methods known in the art and according to manufacturers' recommendations. The "target" proteins, F1 ATP synthase and/or the alpha and/or beta subunits thereof, can be coated overnight onto high binding plastic plates or tubes in humidified containers. In a first round of panning, approximately $2 \times 10^{11}$ phage can be incubated on the protein-coated plate for 60 minutes at room temperature while rocking gently. The plates can then be washed using standard wash solutions. The binding phage can then be collected and amplified following elution using the target protein. Secondary and tertiary pannings can be performed as necessary.

Following the last screening, individual colonies of phage-infected bacteria can be picked at random, the phage DNA isolated and then subjected to dideoxy sequencing. The sequence of the displayed peptides can be deduced from the DNA sequence.

IV. Compositions

Therapeutic, prophylactic and diagnostic compositions containing the compounds described herein typically include one or more active compounds together with a pharmaceutically acceptable excipient, diluent or carrier for in vivo use. Such compositions can be readily prepared by mixing the active compound(s) with the appropriate excipient, diluent or carrier.

Any suitable dosage may be administered. The type of angiogenesis-mediated disorder to be treated (cancer, rheumatoid arthritis, and the like), the compound, the carrier and the amount will vary widely depending on body weight, the severity of the condition being treated and other factors that can be readily evaluated by those of skill in the art. Generally a dosage of between about 1 milligrams (mg) per kilogram (kg) of body weight and about 100 mg per kg of body weight is suitable.

A dosage unit may include a single compound or mixtures thereof with other compounds or other anti-cancer agents, if the composition is used to treat cancer, or other anti-arthritic agents, such as COX-2 inhibitors, if the composition is used to treat rheumatoid arthritis. The dosage unit can also include diluents, extenders, carriers and the like. The unit may be in solid or gel form such as pills, tablets, capsules and the like or in liquid form suitable for oral, rectal, topical, intravenous injection or parenteral administration or injection into or around the tumor The compounds are typically mixed with a pharmaceutically acceptable carrier. This carrier can be a solid or liquid and the type is generally chosen based on the type of administration being used.

The compounds can be administered via any suitable route of administration that is effective in the treatment of the particular angiogenesis-mediated disorder that is being treated. Treatment may be oral, rectal, topical, parenteral or intravenous administration or by injection into the tumor and the like. The method of administering an effective amount also varies depending on the angiogenesis-mediated disorder being treated. It is believed that parenteral treatment by intravenous, subcutaneous, or intramuscular application of the compounds, formulated with an appropriate carrier, additional cancer inhibiting compound or compounds or diluents to facilitate administration, will be the preferred method of administering the compounds.

The compounds can be incorporated into a variety of formulations for therapeutic administration. More particularly, the compounds can be formulated into pharmaceutical compositions by combination with appropriate, pharmaceutically acceptable carriers or diluents, and may be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intratracheal, etc., administration. Moreover, the compounds can be administered in a local rather than systemic manner, for example via injection of the compound directly into a solid tumor, often in a depot or sustained release formulation. In addition, the compounds can be administered in a targeted drug delivery system, for example, in a liposome coated with the antibodies described herein. Such liposomes will be targeted to and taken up selectively by the tumor.

In addition, the compounds can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like.

The compounds can be administered alone, in combination with each other, or they can be used in combination with other known compounds (e.g., other anti-cancer drugs or other drugs, such as anti-inflammatories, antibiotics, corticosteroids, vitamins, etc.). For instance, the compounds can be used in conjunctive therapy with other known anti-angiogenic chemotherapeutic or antineoplastic agents (e.g., vinca alkaloids, antibiotics, antimetabolites, platinum coordination complexes, etc.). For instance, the compounds can be used in conjunctive therapy with a vinca alkaloid compound, such as vinblastine, vincristine, taxol, etc.; an antibiotic, such as adriamycin (doxorubicin), dactinomycin (actinomycin D), daunorubicin (daunomycin, rubidomycin), bleomycin, plicamycin (mithramycin) and mitomycin (mitomycin C), etc.; an antimetabolite, such as methotrexate, cytarabine (AraC), azauridine, azaribine, fluorodeoxyuridine, deoxycoformycin, mercaptopurine, etc.; or a platinum coordination complex, such as cisplatin (cis-DDP), carboplatin, etc. In addition, the compounds can be used in conjunctive therapy with other known anti-angiogenic chemotherapeutic or antineoplastic compounds. In pharmaceutical dosage forms, the compounds may be administered in the form of their pharmaceutically acceptable salts, or they may also be used alone or in appropriate association, as well as in combination with other pharmaceutically active compounds.

Suitable formulations for use in the present invention are found in *Remington's Pharmaceutical Sciences* (Mack Publishing Company, Philadelphia, Pa., 17th ed. (1985)), which is incorporated herein by reference. Moreover, for a brief review of methods for drug delivery, see, Langer, *Science* 249:1527-1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds are preferably formulated for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulator agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds may be employed. Liposomes and emulsions are well known examples of delivery vehicles or carriers for hydrophobic drugs. In a presently preferred embodiment, long-circulating, i.e., stealth, liposomes are employed. Such liposomes are generally described in Woodle, et al., U.S. Pat. No. 5,013,556, the contents of which are hereby incorporated by reference.

The compounds can be encapsulated in a vehicle such as liposomes that facilitates transfer of the bioactive molecules into the targeted tissue, as described, for example, in U.S. Pat. No. 5,879,713 to Roth et al., the contents of which are hereby incorporated by reference. The compounds can be targeted by selecting an encapsulating medium of an appropriate size such that the medium delivers the molecules to a particular target. For example, encapsulating the compounds within microparticles, preferably biocompatible and/or biodegradable microparticles, which are appropriate sized to infiltrate, but remain trapped within, the capillary beds and alveoli of the lungs can be used for targeted delivery to these regions of the body following administration to a patient by infusion or injection.

In a preferred embodiment; the liposome or microparticle has a diameter which is selected to lodge in particular regions of the body. For example, a microparticle selected to lodge in a capillary will typically have a diameter of between 10 and 100, more preferably between 10 and 25, and most preferably, between 15 and 20 microns. Numerous methods are known for preparing liposomes and microparticles of any particular size range. Synthetic methods for forming gel microparticles, or for forming microparticles from molten materials, are known, and include polymerization in emulsion, in sprayed drops, and in separated phases. For solid materials or preformed gels, known methods include wet or dry milling or grinding, pulverization, classification by air jet or sieve, and the like.

Microparticles can be fabricated from different polymers using a variety of different methods known to those skilled in the art. The solvent evaporation technique is described, for example, in E. Mathiowitz, et al, *J. Scanning Microscopy,* 4, 329 (1990); L. R. Beck, et al., *Fertil. Steril.,* 31, 545 (1979); and S. Benita, et al., *J. Pharm. Sci.,* 73, 1721 (1984). The hot-melt microencapsulation technique is described by E. Mathiowitz, et al., *Reactive Polymers,* 6, 275 (1987). The spray drying technique is also well known to those of skill in the art. Spray drying involves dissolving a suitable polymer in an appropriate solvent. A known amount of the compound is suspended (insoluble drugs) or co-dissolved (soluble drugs) in the polymer solution. The solution or the dispersion is then spray-dried. Microparticles ranging between 1-10 microns are obtained with a morphology which depends on the type of polymer used.

Microparticles made of gel-type polymers, such as alginate, can be produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath to allow sufficient time for gelation to occur. Microparticle particle size is controlled by using various size extruders or varying either the nitrogen gas or polymer solution flow rates.

Particle size can be selected according to the method of delivery which is to be used, typically IV injection, and where appropriate, entrapment at the site where release is desired.

Liposomes are available commercially from a variety of suppliers. Alternatively, liposomes can be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

The monoclonal antibodies specific for F1 ATP synthase, in particular, for the alpha and/or beta subunits of F1 ATP synthase as described herein can optionally be conjugated to liposomes and the delivery can be targeted in this manner. In addition, targeting of a marker on abnormal tumor vasculature can be employed. The targeting moiety when coupled to a toxic drug or radioisotope will act to concentrate the drug where it is needed. Ligands for tumor-associated vessel markers can also be used. For example, a cell adhesion molecule that binds to a tumor vascular element surface marker can be employed. Liposomes and other drug delivery systems can also be used, especially if their surface contains a ligand to direct the carrier preferentially to the tumor vasculature. Liposomes offer the added advantage of shielding the drug from most normal tissues. When coated with polyethylene glycol (PEG) (i.e., stealth liposomes) to minimize uptake by phagocytes and with a tumor vasculature-specific targeting moiety, liposomes offer longer plasma half-lives, lower non-target tissue toxicity, and increased efficacy over non-targeted drug. Using the foregoing methods, the compounds can be targeted to the tumor vasculature to effect control of tumor progression or to other sites of interest (e.g., endothelial cells).

Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few days up to over 100 days. Such sustained release capsules typically include biodegradable polymers, such as polylactides, polyglycolides, polycaprolactones and copolymers thereof.

Pharmaceutical compositions suitable for use in the methods described herein include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

Therapeutically effective dosages for the compounds described herein can be estimated initially from cell culture assays. For example, a dose can be formulated in animal models to achieve a circulating concentration range that includes the $IC_{50}$ as determined in cell culture (i.e., the concentration of test compound that is lethal to 50% of a cell culture), or the $IC_{100}$ as determined in cell culture (i.e., the concentration of compound that is lethal to 100% of a cell culture). Such information can be used to more accurately determine useful doses in humans. Initial dosages can also be estimated from in vivo data.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, p. 1).

Dosage amount and interval may be adjusted individually to provide plasma levels of the active compound which are sufficient to maintain therapeutic effect. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

While the composition may be administered by routes other than intravenously (i.v.), intravenous administration is preferred. This is because the target of the therapy is primarily the proliferating vasculature comprising the angiogenesis; and thus, administering the composition intravenously saturates the targeted vasculature much quicker than if another route of administration is used. Additionally, the intravenous route allows for the possibility of further targeting to specific tissues.

In one embodiment, a catheter is used to direct the composition directly to the location of the target angiogenesis. For example, if tumor angiogenesis is the target of the anti-angiogenic therapy, and if the tumor is located in the liver, then the immunoconjugate or the unconjugated antibody or a fragment thereof may be delivered into the hepatic portal vein using a catheter. In this embodiment, systemic distribution of composition is minimized, further minimizing any potential side effects from the antiangiogenic therapy.

V. Screening Methods

Various screening methods can be used to determine the ability of compounds to inhibit the binding of angiostatin to the alpha and/or beta subunits of F1 ATP synthase. In the methods described herein, compounds can bind to a position on the alpha or beta subunits and inhibit angiostatin binding. Such compounds can act as agonists, partial agonists, inverse agonists or antagonists. The mere fact that they inhibit angiostatin binding does not determine their ultimate effect on ATP synthase.

Various other screening methods can also be used to determine the activity of compounds bound to the alpha and/or beta subunits of F1 ATP synthase as agonists, partial agonists, inverse agonists, antagonists, allosteric promoters and inhibitors. Examples of suitable screening methods include measuring ATP synthesis and measuring the cellular proliferation of human vascular endothelial cells (HUVEC).

The compounds can be evaluated using in vitro assays to determine their biological activity. These assays are familiar to those skilled in the art and include HUVEC and BCE proliferation assays, HUVEC wound/migration assay, endothelial cell tube forming assay, CAM assay, Matrigel™ invasion assay and the rat aortic assay. The ability of a compound to inhibit or promote angiogenesis in these assays would indicate that the compound is either able to mimic the interaction of angiostatin with F1 ATP synthase or the alpha and/or beta subunits thereof, or function in an allosteric fashion.

The biological activity of the compounds may also be tested in vivo. Examples of suitable assays include the B16B16 metastasis assay or the Lewis Lung Carcinoma primary tumor or metastasis assays. In such experiments, the activity of the compounds can be compared to that of angiostatin if desired.

Suitable binding assays are described in more detail below.

VI. Binding Assays

ATP synthase includes two principal domains, an asymmetric membrane-spanning Fo portion containing a proton channel and a soluble F1 portion containing three catalytic sites that cooperate in synthetic reactions. The F1 region includes subunits alpha, beta, gamma and delta. (See Elston et al., Nature 391:510 (1998).) The entire ATP synthase molecule can be used in the present assays or a subunit thereof can be used, for example, the alpha and/or beta subunit, the angiostatin binding domain of ATP synthase can also be used, as can a fusion protein comprising the synthase, the subunit thereof or the angiostatin binding domain thereof. The Examples that follow indicate that the alpha and beta subunits of ATP synthase are present on the plasma membrane of endothelial cells. Further, the Examples indicate that angiostatin binds the alpha and/or beta subunits. The alpha and/or beta subunits present on cellular plasma membranes may be identical to those present on mitochondrial membranes or they may represent a truncated (e.g., N- or C-terminal truncated) form thereof.

The binding assays described herein can use any such truncated forms of the alpha or beta subunits. Binding assays include cell-free assays in which ATP synthase or the alpha and/or beta or subunit thereof or angiostatin binding domain thereof (or fusion protein containing same) is incubated with a test compound (proteinaceous or non-proteinaceous) which, advantageously, bears a detectable label (e.g., a radioactive or fluorescent label). Following incubation, the ATP synthase or alpha and/or beta subunit thereof or angiostatin binding domain thereof (or fusion protein), free or bound to test compound, can be separated from unbound test compound using any of a variety of techniques. For example, the ATP synthase (or subunit or binding domain of fusion protein) can be bound to a solid support (e.g., a plate or a column) and washed free of unbound test compound. The amount of test compound bound to ATP synthase or alpha and/or beta subunit thereof or angiostatin binding domain thereof (or fusion protein), is then determined, for example, using a technique appropriate for detecting the label used (e.g., liquid scintillation counting and gamma counting in the case of a radiolabeled test compound or by fluorometric analysis).

Binding assays can also take the form of cell-free competition binding assays. In such assays, ATP synthase or the alpha and/or beta subunit thereof or angiostatin binding domain thereof, or fusion protein containing same, is incubated with a compound known to interact with F1 ATP synthase, in particular, the alpha and/or beta subunits thereof, which compound, advantageously, bears a detectable label (e.g., a radioactive or fluorescent label). A test compound (proteinaceous or non-proteinaceous) is added to the reaction and assayed for its ability to compete with the known (labeled) compound for binding to F1 ATP synthase or the alpha and/or beta subunit thereof or angiostatin binding domain thereof (or fusion protein).

Free known (labeled) compound can be separated from bound known compound, and the amount of bound known compound determined to assess the ability of the test compound to compete. This assay can be formatted so as to facilitate screening of large numbers of test compounds by linking the ATP synthase or alpha and/or beta subunit thereof or angiostatin binding domain thereof (or fusion protein), to a solid support so that it can be readily washed free of unbound reactants. A plastic support, for example, a plastic plate (e.g., a 96 well dish), is preferred. ATP synthase or alpha and/or beta subunit thereof or angiostatin binding domain thereof (or fusion protein), suitable for use in the cell-free assays described above can be isolated from natural sources (e.g., membrane preparations) or prepared recombinantly or chemically. The ATP synthase or alpha and/or beta subunit thereof or angiostatin binding domain thereof, can be prepared as a fusion protein using, for example, known recombinant techniques. Preferred fusion proteins include a GST (glutathione-S-transferase) moiety, a GFP (green fluorescent protein) moiety (useful for cellular localization studies) or a His tag (useful for affinity purification). The non-ATP synthase moiety can be present in the fusion protein N-terminal or C-terminal to the ATP synthase, subunit or binding domain.

As indicated above, the ATP synthase or alpha and/or beta subunit thereof or angiostatin binding domain thereof, or fusion protein, can be present linked to a solid support, including a plastic or glass plate or bead, a chromatographic resin (e.g., Sepharose), a filter or a membrane. Methods for attaching proteins to such supports are well known in the art and include direct chemical attachment and attachment via a binding pair (e.g., biotin and avidin or biotin and streptavidin). Whether free or bound to a solid support, the F1 ATP synthase or alpha and/or beta subunit thereof or angiostatin binding domain thereof, or fusion protein, can be unlabeled or can bear a detectable label (e.g., a fluorescent or radioactive label).

The binding assays also include cell-based assays in which F1 ATP synthase or alpha and/or beta subunit thereof or angiostatin binding domain thereof or fusion protein, is presented on a cell surface. Cells suitable for use in such assays include cells that naturally express F1 ATP synthase and cells that have been engineered to express F1 ATP synthase (or subunit thereof or angiostatin binding domain thereof or fusion protein comprising same). The cells can be normal or tumorigenic. Advantageously, cells expressing human ATP synthase are used. Examples of suitable cells include procaryotic cells (e.g., bacterial cells (e.g., E. coli)), lower eucaryotic cells, yeast cells (e.g., hybrid kits from Promega (CG 1945 and Y190), and the strains YPH500 and BJ5457)) and higher eucaryotic cells (e.g., insect cells and mammalian cells (e.g., endothelial cells, including bovine aortic endothelial cells (BAEC), bovine adrenal medulla endothelial cells (BAMEC), murine endothelial cells od-1, HUVEC or any human endothelial cell line, or cells such as human lung carcinoma cells (e.g., A549 cells)).

Cells can be engineered to express F1 ATP synthase (advantageously, human F1 ATP synthase or the alpha and/or beta subunit thereof or angiostatin binding domain thereof, or fusion protein that includes same) by introducing into a selected host an expression construct comprising a sequence encoding F1 ATP synthase, or subunit thereof or angiostatin binding domain thereof or fusion protein, operably linked to a promoter. A variety of vectors and promoters can be used. For example, pET-24a(+) (Novagen) containing a T7 promoter is suitable for use in bacteria, likewise, pGEX-5X-1. Suitable yeast expression vectors include pYES2 (Invitron). Suitable baculovirus expression vectors include p2Bac (Invitron). Suitable mammalian expression vectors include pBK/CMV (Stratagene). Introduction of the construct into the host can be effected using any of a variety of standard transfection/transformation protocols (see *Molecular Biology, A Laboratory Manual, second edition, J. Sambrook, E. F. Fritsch and T. Maniatis, Cold Spring Harbor Press,* 1989). Cells thus produced can be cultured using established culture techniques suitable for the involved host. Culture conditions can be optimized to ensure expression of the F1 ATP synthase (or subunit, binding domain or fusion protein) encoding sequence. While for the cell-based binding assays the ATP synthase (or subunit, binding domain or fusion protein) can be expressed on a host cell membrane (e.g., on the surface of the host cell), for other purposes the encoding sequence can be selected so as to ensure that the expression product is secreted into the culture medium. The cell-based binding assays described herein can be carried out by adding test compound (advantageously, bearing a detectable (e.g., radioactive or fluorescent) label), to medium in which the F1 ATP synthase (or alpha and/or beta subunit thereof or angiostatin binding domain thereof or fusion protein containing same) expressing cells are cultured, incubating the test compound with the cells under conditions favorable to binding and then removing unbound test compound and determining the amount of test compound associated with the cells.

F1 ATP synthase on a cell membrane (e.g., on the cell surface) can be identified using techniques such as those in the Examples that follow (e.g., the cell surface can be biotin labeled and the protein followed by a fluorescent tag). Membrane associated proteins (e.g., cell surface proteins) can also be analyzed on a Western blot and the bands subjected to mass spectroscopy analysis. For example, a fluorescently tagged antibody can be used, and the cells can then be probed with another fluorescently tagged protein. Each tag can be monitored at a different wavelength, for example, using a confocal microscope to demonstrate co-localization.

As in the case of the cell-free assays, the cell-based assays can also take the form of competitive assays wherein a compound known to bind F1 ATP synthase (and preferably labeled with a detectable label) is incubated with the F1 ATP synthase (or subunit thereof or angiostatin binding domain thereof or fusion protein comprising same) expressing cells in the presence and absence of test compound. The affinity of a test compound for F1 ATP synthase can be assessed by determining the amount of known compound associated with the cells incubated in the presence of the test compound, as compared to the amount associated with the cells in the absence of the test compound.

The selectivity of a test compound for cell surface F1 ATP synthase, in particular, for the alpha and/or beta subunits thereof, as compared to mitochondrial F1 ATP synthase, can be easily assessed. Compounds which, by virtue of their physicochemical properties, cannot diffuse across cellular membranes (and that are not natural or artificial ligands for cell transporters) can be considered selective for cell surface F1ATP synthase. For example, compounds that bind cell surface F1 ATP synthase but are positively charged can thereby be prevented from diffusing across membranes.

A test compound identified in one or more of the above-described assays as being capable of binding to F1 ATP synthase, and, particularly, to the alpha and/or beta subunits thereof, can, potentially, promote or inhibit angiogenesis, cellular migration, proliferation and pericellular proteolysis and, potentially, inhibit the ability of angiostatin to bind its receptor (the alpha and/or beta subunits of F1 ATP synthase). To determine the specific effect of any particular test compound selected on the basis of its ability to bind the alpha and/or beta subunits of F1 ATP synthase (or inhibit (competitively or non-competitively) angiostatin binding to ATP synthase), assays can be conducted to determine, for example, the effect of various concentrations of the selected test compound on activity, for example, cell (e.g., endothelial cell) proliferation, metabolism or cytosolic/cytoplasmic pH. (Assays can be conducted to determine the effect of test compounds on F1 ATP synthase (and F1 ATPase) activity using standard enzyme assay protocols.)

Cell proliferation can be monitored by measuring uptake of labeled bases into cellular nucleic acids, for example, radioactively (e.g., $^3$H, SiC, $^{14}$C), fluorescently (e.g., CYQUANT (Molecular Probes)) or colorimetrically (e.g., BrdU (Boehringer-Mannheim or MTS (Promega)). Cytosolic/cytoplasmic pH determinations can be made with a digital imaging microscope using substrates such as BCECF (bis(carboxyethyl)-carbonyl fluorescein) (Molecular Probes, Inc.). A test compound that reduces or replaces the concentration of angiostatin required to inhibit cellular proliferation or lower intracellular pH can be expected to do so by acting as an angiostatin agonist. A test compound that enhances cellular proliferation in the presence of angiostatin (or functional portion thereof or functional equivalent thereof) can be expected to do so by acting as an angiostatin antagonist or allosteric inhibitor. A test compound that raises intracellular pH in the presence of angiostatin (or functional portion thereof or functional equivalent thereof) may do so by acting as an angiostatin antagonist. These functional assays can also be conducted in the absence of angiostatin (i.e., test compound alone), with angiostatin (or functional portion thereof or functional equivalent thereof) run as a separate control. A test compound that, for example, modulates intracellular pH in the absence of angiostatin can be an angiostatin agonist, partial agonist, inverse agonist or antagonist.

Other types of assays that can be carried out to determine the effect of a test compound on angiostatin binding to F1 ATP synthase include the Lewis Lung Carcinoma assay (O'Reilly et al., Cell 79:315 (1994)) and extracellular migration assays (Boyden Chamber assay: Kleinman et al., Biochemistry 25:312 (1986) and Albini et al., Can. Res. 47:3239 (1987)). Das et al. (J. Exp. Med. 180:273 (1994)) have reported the presence of the beta subunit of H+ transporting F1 ATP synthase on the plasma membrane of human tumor cell lines. The present demonstration of the alpha and/or beta subunit of F1 ATP synthase on plasma membranes, and the binding thereto by angiostatin, indicates that angiostatin may be directly involved in effecting cytolysis, for example, of tumor cells. The binding of angiostatin to its receptor may result in the transport of protons across plasma membranes and into cells with the result being cytolysis by osmotic shock.

Accordingly, the methods permit the screening of compounds for their ability to modulate the effect of angiostatin on proton pumping that results from the binding of angiostatin to F1 ATP synthase, in particular, to the alpha and/or beta subunits thereof. In one such assay, cells that express F1 ATP synthase (or the alpha and/or beta subunit or portion thereof) are incubated with the test compound in the presence of angiostatin (or functional portion thereof or functional equivalent thereof) and the influx of protons into the cells determined and compared to the influx of protons observed in the absence of the test compound. Compounds that reduce the concentration of angiostatin (or functional portion thereof or functional equivalent thereof) necessary to effect a particular level of proton influx can be expected to do so by acting as a angiostatin agonist. Compounds that reduce the amount of angiostatin-induced proton pumping observed can be expected to do so by acting as an angiostatin antagonist. The amount of proton pumping can be determined using any of a variety of approaches, including using cells preloaded with a pH sensitive reporter and monitoring the effect of the test compound on the reporter. For example, BCECF can be used to measure pH (Misra et al., Biochem. J. 309:151 (1995)). Alternatively, the effect of a test compound on proton pumping can be determined by monitoring cell lysis using, for example, a chromium 51 release assay (McManus et al., Exper. Lund Res. 15:849 (1989); Zucker et al., Res. Comm. Chem. Path. Pharm. 39:321 (1983)).

In addition to the various approaches described above, assays can also be designed so as to be monitorable colorometrically or using time-resolved fluorescence.

In another embodiment, the invention relates to compounds identified using the above-described assays as being capable of binding to F1 ATP synthase (and/or inhibiting angiostatin from binding to F1 ATP synthase (competively or non-competitively) and/or modulating the angiostatin effects on cellular bioactivities and/or modulating F1 ATP synthase activity. Such compounds can include novel small molecules (e.g., organic compounds (for example, organic compounds less than 500 Daltons), and novel polypeptides, oligonucleotides, as well as novel natural products (preferably in isolated form) (including alkyloids, tannins, glycosides, lipids, carbohydrates and the like). Compounds that bind to the alpha and/or beta subunits of F1 ATP synthase can be used to inhibit angiogenesis, for example, in tumor bearing patients and in patients suffering from vascular related retinopathies (including diabetic) and Terigium.

In one embodiment, the screens first determine the binding affinity of the compound for the target, then look at the biochemical activity of the compounds, then look at cell-based or in vivo activity. An analysis of angiostatin binding or inhibition thereof can then be performed to map possible binding sites or for a compulsive validation, but are in no way necessary to develop an effective anti-angiogenic drug.

There are two presently preferred screening assays, each used to used to screen peptide phage display libraries. In one embodiment, purified $F_1$ complex is coated onto high binding plastic surfaces of microtiter plates or Nunc-Immuno™ Tubes. Nonspecific protein binding surfaces are blocked by incubation with a blocking solution containing BSA, milk, or another complex protein mixture. Unbound $F_1$ and excess block are washed away and replaced by buffer. A phage library is contacted with the target and then unbound phage are washed away. Bound phage are eluted by target denaturation or by cleavage. The population of selected phage are then contacted with bacterial cells to achieve phage infection of these cells. Infected cultures are harvested after several hours of infection and phage recovered by centrifugation. Such phage are then used as input for an additional round of selection as described above. Typically three to five rounds of infection are performed to obtain a highly enriched subpopulation of the original library with affinity for $F_1$ complex. Individual phage are isolated by plaque assay of limiting dilutions and then characterized as individual species. Such purified phage species may be subjected to DNA sequencing in order to infer the sequence of their encoded peptides or antibodies. In addition, the phage may be assayed for their affinity to the purified $F_1$ complex or for their ability to inhibit $F_1$ activity. Alternatively, the peptides may be prepared as synthetic chemicals using solid phase peptide synthesis, or may be expressed recombinantly as fusion proteins, and then assayed in either of these forms.

In a second embodiment, the target is screened as a native enzyme complex on the surface of endothelial cells. Cultured endothelial cells are prepared in chamber slides and then blocked with BSA or milk as described above. The phage library is contacted with the target and then unbound phage are washed away. At this point, many phage species remained bound to the cell surface, with only a minority actually bound to the native $F_1$ complex. The phage of interest are selectively labeled by a biotinylation reaction mediated by horse radish peroxidase (HRP) that is tethered to an $F_1$ subunit-specific antibody. Thus, an anti-α-subunit monoclonal antibody is prepared as an HRP conjugate and then contacted with the endothelial cells bearing specifically-bound phage. Unbound antibodies are removed by washing. The remaining antibodies are thus bound in close proximity to the phage that are bound to $F_1$, but not to phage binding other cell surface targets. Phage in proximity to the HRP conjugate are then biotinylated by adding biotin-tyramine and hydrogen peroxide according to the method of Osbourn et al. (Osbourn et al., (1998). Pathfinder selection: in situ isolation of novel antibodies. *Immunotechnology* 3, 293-302; Osbourn et al., (1998) Directed selection of MIP-1 alpha neutralizing CCR5 antibodies from a phage display human antibody library. *Nat Biotechnol* 16, 778-81.). All phage are eluted as described above and the biotinylated phage are then recovered by passage over streptavidin beads (Dynal Biotech, New York). Active phage are then recovered by infection and amplified as above.

In both types of screens, we typically use high complexity libraries for our initial screens. Once peptide sequences are obtained, consensus sequences are sought in multiple sequence alignments and efforts are made to determine a structure-activity relationship in which the activity may be binding affinity or ability to inhibit the enzymatic activity. The consensus information is then used to construct a focused motif library that is rescreened as described above to derive high affinity ligands with high potential for modulating bioactivity of the target.

The compounds identified in accordance with the above assays can be formulated as pharmaceutical compositions.

VII. Kits

Kits suitable for conducting the assays described herein can be prepared. Such kits can include F1 ATP synthase or the alpha and/or beta or other subunits thereof, or angiostatin binding domain thereof, or fusion protein comprising same, and/or angiostatin. These components can bear a detectable label. The kit can include an ATP synthase-specific or angiostatin-specific antibody. Plasminogen can also be present.

The kit can include any of the above components disposed within one or more container means. The kit can further include ancillary reagents (e.g., buffers) for use in the assays. Diagnostic methods based on the assays for binding angiostatin to ATP synthase can be used to identify patients suffering from angiogenesis-mediated disorders. The demonstration that ATP synthase is the angiostatin binding protein, and the resulting availability of methods of identifying agents that can be used to modulate the effects of angiostatin, make it possible to determine which individuals will likely be responsive to particular therapeutic strategies. Treatment strategies for individuals suffering from angiogenesis-mediated disorders can be designed more effectively and with greater predictability of a successful result. Thus, for a given angiogenesis-mediated disorder that is of polygenic (non-Mendelian) origin, one would select that genotype that is implicated not only in the disease, but also in that variant of the disease that is associated with abnormal angiogenesis and proceed to screen, via a diagnostic procedure, all future patients having the same genotype in order to choose that therapeutic strategy most associated with a successful outcome or least associated with a toxic side effect, for that genotype.

The present invention will be better understood with reference to the following non-limiting examples.

EXAMPLE 1

Angiostatin Binds ATP Synthase on the Surface of Human Endothelial Cells

Summary: Angiostatin, a proteolytic fragment of plasminogen, is a potent antagonist of angiogenesis and an inhibitor of endothelial cell migration and proliferation. To determine whether the mechanism by which angiostatin inhibits endothelial cell migration and/or proliferation involves binding to cell surface plasminogen receptors, the binding proteins for plasminogen and angiostatin were isolated from human umbilical vein endothelial cells. Binding studies demonstrated that plasminogen and angiostatin bound in a concentration-dependent, saturable manner. Plasminogen binding was unaffected by a 100-fold molar excess of angiostatin, indicating the presence of a distinct angiostatin binding site. The finding was confirmed by ligand blot analysis of isolated human umbilical vein endothelial cell plasma membrane fractions, which demonstrated that plasminogen bound to a 44-kDa protein, whereas angiostatin bound to a 55-kDa species. Amino-terminal sequencing coupled with peptide mass fingerprinting and immunologic analyses identified the plasminogen binding protein as annexin II and the angiostatin binding protein as the alpha/beta-subunits of ATP synthase. The presence of this protein on the cell surface was confirmed by flow cytometry and immunofluorescence analysis. Angiostatin also bound to the recombinant alpha-subunit of human ATP synthase, and this binding was not inhibited by a 2,500-fold molar excess of plasminogen. Angiostatin's antiproliferative effect on endothelial cells was inhibited by as much as 90% in the presence of anti-alpha-subunit ATP synthase antibody. Binding of angiostatin to the alpha/beta-subunits of ATP synthase on the cell surface may mediate its antiangiogenic effects and the down-regulation of endothelial cell proliferation and migration.

Tumor growth requires the continuous and persistent generation of blood vessels. If this angiogenesis is prevented, tumor growth is dramatically impaired and the tumor size is restricted. Endogenous angiogenic inhibitors therefore are likely to play an important role in tumor development. Angiostatin, a proteolytic fragment of plasminogen, is a potent inhibitor of angiogenesis and the growth of tumor cell metastases (O'Reilly, M. S., Holmgren, L., Shing, Y., Chen, C., Rosenthal, R. A., Moses, M., Lane, W. S., Cao, Y., Sage, E. H. & Folkman, J. (1994) Cell 79, 315-328). Angiostatin can be generated in vitro by limited proteolysis of plasminogen (Sottrup-Jensen, L., Claeys, H., Zajdel, M., Petersen, T. E. & Magnusson, S. (1978) Prog. Chem. Fibrinolysis Thrombolysis 3, 191-209), resulting in a 38-kDa plasminogen fragment containing kringles 1-3. Although the enzymatic mechanism by which angiostatin is generated in vivo is unknown, recent studies have demonstrated that the cleavage of plasminogen to yield angiostatin can be catalyzed by a serine proteinase (Gately, S., Twardowski, P., Stack, M. S., Patrick, M., Boggio, L., Cundiff, D. L., Schnaper, H. W., Madison, L., Volpert, O., Bouck, N., et al. (1996) Cancer Res. 36, 4887-4890), a macrophage metalloelastase (Dong, Z., Kumar, R., Yang, X. & Fidler, I. J. (1997) Cell 88, 801-810), and matrix metalloproteinase 3 (MMP-3 or stomelysins 1) (Lijnen, H. R., Ugwu, F. & Collen, D. (1998) Biochemistry 37, 4699-4702). Generation of angiostatin from reduction of plasmin also has been shown in vitro with human prostate carcinoma cells (Gately, S., Twardowski, P., Stack, M. S., Cundiff, D., Grella, D., Castellino, F. J., Enghild, J., Kwaan, H. C., Lee, F., Kramer, R. A., et al. (1997) Proc. Natl. Acad. Sci. USA 94, 10868-10872), Chinese hamster ovary cells (Stathakis, P., Fitzgerald, M., Matthias, L. J., Chesterman, C. N. & Hogg, P. J. (1997) J. Biol. Chem. 272, 20641-20645), and human fibrosarcoma cells (Stathakis, P., Fitzgerald, M., Matthias, L. J., Chesterman, C. N. & Hogg, P. J. (1997) J. Biol. Chem. 272, 20641-20645). Additional studies demonstrated suppression of primary tumor growth in mice injected with purified angiostatin, with evidence of increased tumor-specific apoptosis (O'Reilly, M. S., Holmgren, L., Chen, C. & Folkman, J. (1996) Nat. Med. 2, 689-692). The antiproliferative effect of angiostatin also may result from inhibition of cell cycle progression (Griscelli, F., Li, H., Bennaceur-Griscelli, A., Soria, J., Opolon, P., Soria, C., Perricaudet, M., Yah, P. & Lu, H. (1998) Proc. Natl. Acad. Sci. USA 95, 6367-6372). However, little is known about the molecular mechanism(s) by which angiostatin functions to regulate endothelial cell behavior.

Cellular receptors for plasminogen, including annexin II and actin, are found on human umbilical vein endothelial cells (HUVEC) and are believed to function in the regulation of endothelial cell activities, including angiogenesis (Hajjar, K. A., Harpel, P. C., Jaffe, E. A. & Nachman, R. L. (1986) J. Biol. Chem. 261, 11656-11662; Hajjar, K. A., Jacovina, A. T. & Chacko, J. (1994) J. Biol. Chem. 269, 21191-21197). Receptors for plasminogen also are expressed in high numbers on tumor cells where they have been identified as critical for tumor invasion. Proteins normally found in the cytoplasm, such as alpha-enolase (Miles, L. A., Dahlberg, C. M., Plescia, J., Felez, J., Kato, K. & Plow, E. F. (1991) Biochemistry 30, 1682-1691) and ATP synthase (Das, B., Mondragon, M. O. H., Sadeghian, M., Hatcher, V. B. & Norin, A. J. (1994) J. Exp. Med. 180, 273-281), also occur on the cell surface and function to bind plasminogen or aid in lymphocyte-mediated cytotoxicity, respectively. The beta-subunit of mitochondrial ATP synthase is present on the surface of several tumor cell lines and may function to transport H+ across the plasma membrane, resulting in cytolysis. This finding is supported by studies demonstrating addition of ATP synthase to cultures of tumor cell lines induces membrane depolarization, changes in permeability, and eventual lysis of a variety of transformed cells (Virgilio, F. D., Pizzo, P., Zanovello, P., Bronte, V. & Collavo, D. (1990) Immunol. Today 11, 274-277; Rozengurt, E., Heppel, L. A. & Friedberg, I. (1977) J. Biol. Chem. 252, 4584-4590; Rozengurt, E. & Heppel, L. (1979) J. Biol. Chem. 254, 708-714; Chahwala, S. B. & Cantley, L. C. (1984) J. Biol. Chem. 259, 13717-13722; Saribas, A. S., Lustig, K. D., Zhang, X. K. & Weisman, G. A. (1993) Anal. Biochem. 209, 45-52; Virgilio, F. D., Bronte, V., Collavo, D. & Zanovello, P. (1989) J. Immunol. 143, 1955-1960; Zanovello, P., Bronte, V., Rosato, A., Pizzo, P. & Virgilio, F. D. (1990) J. Immunol. 145, 1545-1550). The presence of ATP synthase on tumor cells may help explain lymphocyte-mediated destruction of tumors.

This example focused on the interaction of plasminogen and angiostatin with HUVEC. Angiostatin did not compete for plasminogen binding to the endothelial cells, suggesting the presence of distinct binding sites for each protein on the cell surface. Further studies identified the angiostatin binding site on HUVEC as the alpha/beta-subunits of ATP synthase (alpha/beta-ATP synthase). Binding to alpha/beta-ATP synthase was confirmed by using peptide mass fingerprinting, flow cytometry, immunohistochemical staining, Western blotting, competitive cellular binding, and proliferation assays. These studies present evidence for the identification of the alpha/beta-ATP synthase on the endothelial cell surface and imply a potential regulatory role for plasma membrane ATP synthase in endothelial cell proliferation and migration.

Materials and Methods

Protein Purification. Plasminogen was purified from human plasma by affinity chromatography and separated into isoforms 1 and 2 as described (Deutsch, D. & Mertz, E. T. (1970) Science 170, 1095-1096; Gonzalez-Gronow, M. & Robbins, K. C. (1984) Biochemistry 23, 190-194). Based on kinetic and electrophoretic analysis, all plasminogen preparations were plasmin-free. The concentration of plasminogen was determined spectrophotometrically at a wavelength of 280 nm by using an $A_1\%/1$ cm value of 1.67 and a molecular mass of 92 kDa for Glu1-plasminogen (Castellino, F. J. (1981) Chem. Rev. 81, 431-436). Human plasminogen kringles 1-3 (angiostatin) were purified as described (Sottrup-Jensen, L., Claeys, H., Zajdel, M., Petersen, T. E. & Magnusson, S. (1978) Prog. Chem. Fibrinolysis Thrombolysis 3, 191-209). The concentration of angiostatin was determined spectrophotometrically at a wavelength of 280 nm by using an $A_1\%/1$ cm value of 0.8 and a molecular mass of 38 kDa (Sottrup-Jensen, L., Claeys, H., Zajdel, M., Petersen, T. E. & Magnusson, S. (1978) Prog. Chem. Fibrinolysis Thrombolysis 3, 191-209). Protein endotoxin levels were <50.0 pg endotoxin/ml as assessed by Pyrotell *Limulus amebocyte* lysate clotting times (Associates of Cape Cod).

Cell Culture. Primary HUVEC were grown as described (Morales, D. E., McGowan, K. A., Grant, D. S., Maheshwari, S., Bhartiya, D., Cid, M. C., Kleinman, H. K. & Schnaper, H. W. (1995) Circulation 91, 755-763) in 150-mm Petri dishes and retained for up to six passages. Human dermal microvascular endothelial cells were obtained from Clonetics (San Diego), grown according to specifications, and retained for up to six passages. A549 (human lung carcinoma) cells were obtained from the American Type Culture Collection and grown according to specifications. For all experiments, cells were detached by incubation with PBS containing 2 mM EDTA, pH 7.4.

Antibody Purification. Antibody to His-tagged recombinant alpha-subunit ATP synthase was generated in rabbits by intranodal injection (Covance Laboratories, Vienna, Va.). Production bleeds were centrifuged, and the serum obtained was ammonium sulfate precipitated. The precipitate was resuspended in PBS/0.5 M NaCl, pH 7.5, and passed over protein. A-Sepharose (Sigma), plasminogen-Sepharose, and alpha-subunit ATP synthase-Sepharose columns (CNBr coupling, Amersham Pharmacia). Each column was eluted with 20 mM glycine, pH 2.5. Neutralized IgG fractions were tested by immunodiffusion, ELISA, and Western blotting. Antibody to the anti-alpha-subunit of ATP synthase showed no cross-reactivity with plasminogen or other proteins by Western blot analysis.

Polyclonal antibody obtained from A. E. Senior (Rochester Medical Center, Rochester, N.Y.) directed against the alpha-subunit of ATP synthase from *Escherichia coli* was characterized by ELISA and Western blot analysis and showed no crossreactivity with other proteins in the F1 portion or *E. coli* cell membranes (Perlin, D. S. & Senior, A. E. (1985) Arch. Biochem. Biophys. 236, 603-611; Roa, R., Perlin, D. S. & Senior, A. E. (1985) Arch. Biochem. Biophys. 255, 309-315).

Binding Assays. Ligands were radioiodinated by using Iodobeads (Pierce), repurified on L-lysine-Sepharose, eluted with 100 mM ε-aminocaproic acid, and dialyzed in PBS, pH 7.0 before use in binding assays. HUVEC were plated at a density of 5,000 or 10,000 cells/well and incubated with increasing concentrations of $^{125}$I-labeled ligand in media containing 1% BSA for 1 h at 4° C. in 96-well plates. Wells were washed, and remaining bound radioactivity was quantified by using an LKB 1272 γ-radiation counter. Nonspecific binding was measured in the presence of excess unlabeled ligand.

Membrane Purification. Plasma membrane extracts from N-hydroxysuccinimide-biotin-labeled HUVEC were prepared by 300-psi Parr bomb nitrogen cavitation and ultracentrifugation (Young, T. N., Pizzo, S. V. & Stack, M. S. (1995) J. Biol. Chem. 270, 999-1002). Membrane extracts were incubated with plasminogen-Sepharose or angiostatin-Sepharose columns in an inhibitor mixture buffer (Young, T. N., Pizzo, S. V. & Stack, M. S. (1995) J. Biol. Chem. 270, 999-1002). Each Sepharose column was eluted with 50 mM Tris/100 mM ε-aminocaproic acid, pH 7.5, 50 mM Tris/1 M NaCl, pH 7.5, 50 mM Tris/7% dimethyl sulfoxide, and 20 mM glycine, pH 2.5 to account for all types of binding. The glycine eluates were dialyzed, lyophilized, electrophoresed on 5-15% gradient SDS/PAGE (Laemmli, U. K. (1970) Nature (London) 227, 680-685), and electoblotted onto Immobilon membrane (Matsudaira, P. (1987) J. Biol. Chem. 262, 10035-10038) before experiments to identify plasminogen and angiostatin binding proteins.

Mass Spectrometer Analysis. Plasma membrane proteins were separated on SDS/PAGE gels, and the bands of interest were excised from the gels and digested in situ with trypsin. A portion (1/20) of each sample was analyzed by matrix-assisted laser desorption ionization-MS, and the obtained mass spectrometric peptide maps were used to identify the protein in the owl Protein database release 29.6 (Mann, M., Højrup, P. & Roepstrorff, P. (1993) Biol. Mass Spectrom. 22, 338-345; Pappin, D. J. C., Højrup, P. & Bleasby, A. J. (1993) Curr. Biol. 3, 327-332).

Flow Cytometry. HUVEC and A549 cells were resuspended in ice-cold staining buffer (Hanks' balanced salt solution/1% BSA/0.1% sodium azide) and incubated on ice for 30 min with either rabbit polyclonal antiserum raised against alpha-subunit ATP synthase derived from *E. coli* or pre-immune rabbit serum. Cells were washed with ice-cold staining buffer and pelleted in a microfuge at 4° C. This wash was repeated twice, and the cells were resuspended in ice-cold staining buffer before incubation on ice for 30 min in the dark with goat anti-rabbit IgG conjugated to fluorescein isothiocyanate. After the final wash (as above), the cells were pelleted and fixed in 10% neutral buffered formalin at a density of 1×106 cells/ml. Control experiments were performed by using antibody directed against the alpha subunit of ATP synthase, which was preincubated with a 5-fold molar excess of recombinant alpha-subunit ATP synthase protein. The mean relative fluorescence after excitation at a wavelength of 488 nm was determined for each sample on a FACScan flow cytometer (Becton-Dickenson) and analyzed with cellquest software (Becton-Dickenson).

Immunofluorescence Microscopy. HUVEC and human dermal microvascular endothelial cells were plated at 5×10$^5$ cells/ml on glass coverslips and allowed to adhere overnight. Cells were incubated at 4° C. for 1 h in PBS, pH 7.0 containing 1% BSA with either rabbit polyclonal antiserum raised against the alpha subunit of ATP synthase derived from *E. coli*, pre-immune rabbit serum, pre-immune IgG, or anti-rabbit IgG. Cells were washed and incubated at 4° C. for 1 h in the dark with goat anti-rabbit IgG conjugated to indocarbocyanine (Cy3) before washing and fixing in 4% paraformaldehyde. Immunofluorescence microscopy was performed by using an Olympus BX-60 microscope (Olympus, Lake Success, N.Y.).

Cloning of the alpha-Subunit of ATP Synthase. Poly(A)+ mRNA was isolated from HUVEC by using Oligotex resin (Qiagen). RNA was reverse-transcribed into single-stranded cDNA by using AMV Reverse Transcriptase (Boehringer Mannheim). The alpha subunit of ATP synthase was PCR-amplified by using Expand High Fidelity PCR system (Boehringer Mannheim). The 1.7-kb PCR product was purified from a 0.8% Tris-acetate/EDTA agarose gel by using a QIAEX II gel extraction kit. Restriction enzyme digests of the PCR fragment and vector pLE1 were carried out at 37° C. for 1 h. Both digests were passed over Qiaquick purification columns, then ligated overnight at 16° C. by using T4 DNA ligase. Competent *E. Coli* DH5a (GIBCO/BRL) were transformed with the ligation mixture, plated on 2× Bacto-yeast tryptone (YT) agarose plates, and grown overnight at 37° C. Colonies were screened for the insert by restriction enzyme digestion and DNA sequencing.

Purification of the alpha-Subunit of ATP Synthase. Competent *E. coli* BL21DE3 were transformed with the pET24a (+) vector containing the alpha subunit, plated on 2× Bacto-yeast tryptone (YT) agarose, and grown overnight at 37° C. Twenty milliliters of 2×YT containing 50 mg/ml kanamycin was inoculated with one colony and grown overnight at 37° C. (200 rpm). A 1-liter culture (2×YT, 50 mg/ml kanamycin) was inoculated with 20 ml of the noninduced overnight culture and grown at 37° C. to an OD of 0.6 at a wavelength of 600 nm. Isopropyl thio-beta-d-galactosidase was added to a final concentration of 1 mM and grown for an additional 3 h. Cells were harvested by centrifugation at 8,000 rpm for 10 min and stored overnight at −20° C. Lysates were prepared under denaturing conditions and batch-purified by using Qiagen Ni-NTA agarose. Resulting protein was dialyzed against PBS, pH 7.0 for use in all experiments.

Proliferation Assay. HUVEC were plated at a density of 5,000 cells/well in media depleted of FCS overnight to allow the cells to become quiescent. Fresh media containing FCS were added to the wells along with angiostatin at a final concentration of 0.5, 0.75, and 1.0 mM. In some experiments antibody directed against the alpha subunit of ATP synthase derived from *E. coli* was also added at a dilution of 1:10. MTS/PMS [(3-(4,5-dimethylthiazol-2-yl)-5-(3-carboxymethoxyphenyl)-2-(4-sulfophenyl)-2H-tetrazolium, inner salt/phenazine methosulfate] solution was added after 24 h, and the absorbance of formazan was quantitated on a Thermomax plate reader at a wavelength of 490 nm according to the manufacturer's specifications (Promega). The absorbance values used to calculate the percent proliferation of the cells ranged from 0.81 for untreated, 0.60 for treated, and 0.47 for baseline quiescent cells.

Results and Discussion

Figure 1A:
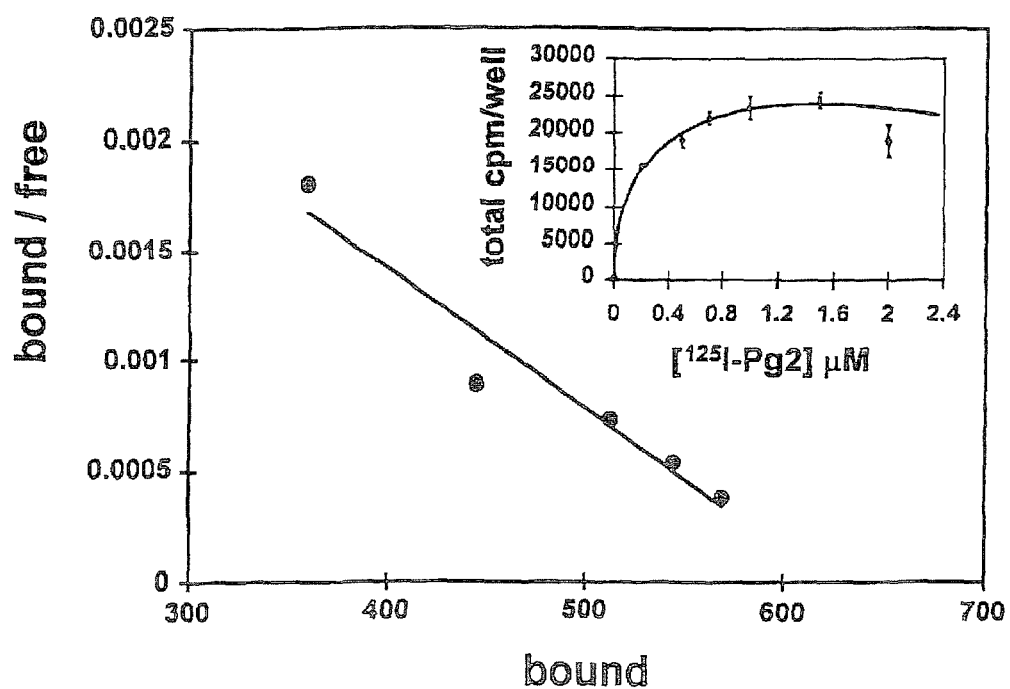
FIGS. 1A and 1B. Direct binding assay and Scatchard analysis of plasminogen and angiostatin with endothelial cells. HUVEC were plated at a density of 10,000 cells/well and incubated with increasing concentrations of $^{125}$I-labeled-plasminogen or angiostatin.
Figure 1B:
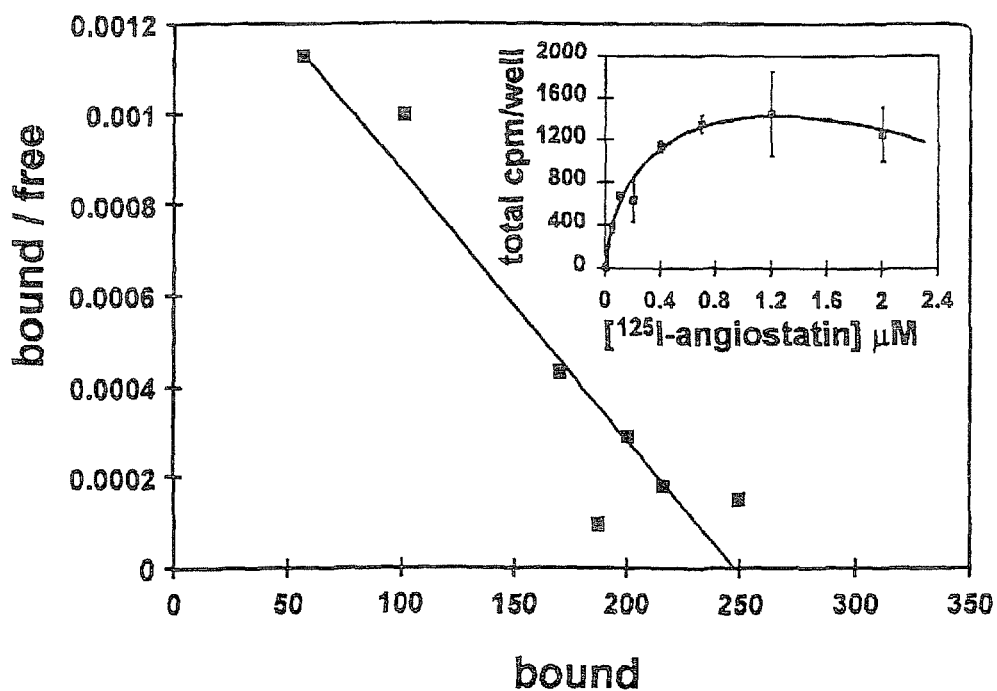
Figure 2:
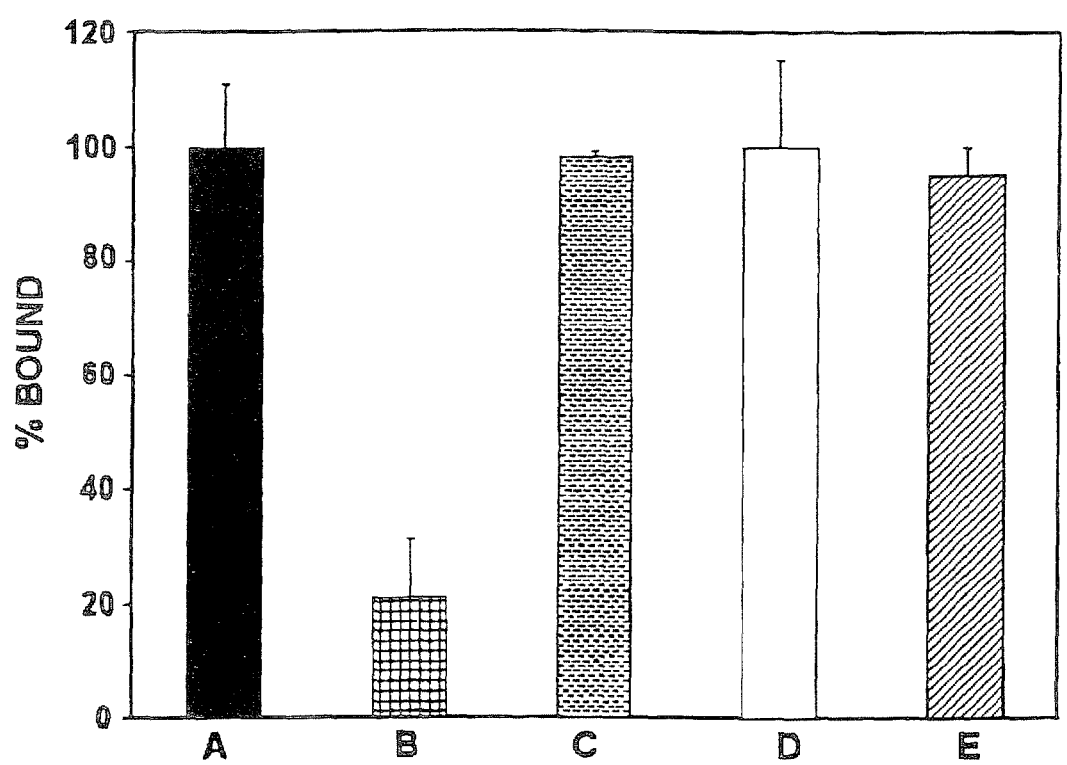
FIG. 2. Competition binding assay between plasminogen and angiostatin. HUVEC were plated at a density of 10,000 cells/well and incubated with 1.0 µM $^{125}$I-labeled plasminogen in the presence of 100-fold molar excess of unlabeled angiostatin for 1 h at 4° C. Cells were washed and the remaining radioactivity, was quantified by γ-counting.

Binding of Plasminogen and Angiostatin to Endothelial Cells. To determine whether angiostatin blocks angiogenesis by competitive interaction with endothelial cell plasminogen receptors, the effects of angiostatin on the binding of plasminogen to endothelial cells were analyzed. In control experiments, plasminogen bound to HUVEC in a concentration-dependent saturable manner with an apparent dissociation constant (Kd) of 158 mM and approximately 870,000 sites per cell (FIG. 1A), comparable to values previously reported (Hajjar, K. A., Jacovina, A. T. & Chacko, J. (1994) J. Biol. Chem. 269, 21191-21197). Angiostatin also bound to HUVEC in a concentration-dependent saturable manner with a similar affinity (Kd of 245 nM), with approximately 38,000 sites per cell (FIG. 1B). Binding studies using $^{125}$I-labeled plasminogen and a 100-fold molar excess of unlabeled angiostatin demonstrated no inhibition of plasminogen binding (FIG. 2). Similar studies were performed by using $^{125}$I-labeled angiostatin. Excess unlabeled plasminogen had little or no effect on angiostatin binding (FIG. 2). In contrast to plasminogen, binding of $^{125}$I-labeled angiostatin to HUVEC in the presence of 100 mM ε-aminocaproic acid was only slightly inhibited, suggesting that binding of angiostatin to endothelial cells is not a lysine binding site-dependent process (data not shown). Together these data suggest the presence of a distinct angiostatin binding site on HUVEC.

Purification of the Angiostatin Binding Site from Endothelial Cells. The cell surface proteins involved in binding of plasminogen or angiostatin to HUVEC were identified by subjecting N-hydroxysuccinimide-biotin-labeled HUVEC plasma membranes to affinity chromatography on plasminogen-Sepharose or angiostatin-Sepharose. Two distinct bands were identified on Western blot analysis using streptavidin-alkaline phosphatase conjugate (FIG. 3A) or by Coomassie brilliant blue stain (FIG. 3C). A companion blot, probed with an antibody to the known plasminogen receptor, annexin II, demonstrated immunologic crossreactivity with the 44-kDa membrane protein isolated from the plasminogen-Sepharose column (FIG. 3B, lane 1), but not with the 55-kDa protein isolated from the angiostatin-Sepharose column (FIG. 3B, lane 2). Ligand blot analysis of the affinity-purified plasma membranes using $^{125}$I-labeled plasminogen (FIG. 3D, lanes 1 and 2) demonstrated binding of plasminogen only to the 44-kDa protein and not to the 55-kDa species, providing additional evidence that HUVEC contain an angiostatin binding site distinct from the known plasminogen binding protein, annexin II.

The proteins were separated on an SDS/PAGE gel, the band of interest was excised from the gel, and then digested in situ with trypsin. Then ½₀ of the sample was analyzed by matrix-assisted laser desorption ionization-MS. The obtained mass spectrometric peptide map was used to identify the alpha/beta-subunits of ATP synthase in the owl Protein database release 29.6 (Mann, M., Højrup, P. & Roepstrorff, P. (1993) Biol. Mass Spectrom. 22, 338-345; Pappin, D. J. C., Højrup, P. & Bleasby, A. J. (1993) Curr. Biol. 3, 327-332). Analysis of protein sequences of alpha and beta ATP synthase from the Institute of Biology and Chemistry of Proteins showed ~23% homology and ~57% similarity.

Peptide Mass Fingerprinting of the Angiostatin Binding Site. To identify the unique angiostatin binding site component, the affinity-purified binding proteins were analyzed by amino-terminal sequencing, mass spectrometer analysis, and peptide mass fingerprinting. Both the 44- and 55-kDa proteins were analyzed by reduced SDS/PAGE and digested with trypsin in situ (Matsui, N. M., Smith, D. M., Clauser, K. R., Fichmann, J., Andrews, L. E., Sullivan, C. M., Burlingame, A. L. & Epstein, L. B. (1997) Electrophoresis 18, 409-417). The resulting peptides were extracted and the mass of approximately 30 peptides was determined by using a Bruker Reflex matrix-assisted laser desorption ionization-time of flight mass spectrometer, providing a unique signature by which to identify the protein by peptide mass searches. The 55-kDa angiostatin binding membrane protein was identified as the alpha/beta-subunits of ATP synthase (Table 1), whereas the plasminogen binding protein was confirmed as annexin H. Although expression of the beta-subunit of ATP synthase has been reported on the surface of several tumor cell lines (Das, B., Mondragon, M. O. H., Sadeghian, M., Hatcher, V. B. & Norin, A. J. (1994) J. Exp. Med. 180, 273-281), evidence is provided herein for surface expression of the alpha/beta-subunits of ATP synthase on HUVEC.

TABLE 1

Bruker Reflex Matrix-assisted laser desorption ionization-time of flight mass spectrometer analysis of 55-kDa peptides

| Sequence | Peptide Mass (monoisotopic) | |
|---|---|---|
| | Measured (Da) | Calculated (Da) |
| QMSLLLR | 859.48 | 859.495 |
| AVDSLVPIGR | 1025.58 | 1025.587 |
| VGLKAPGIIPR | 1119.68 | 1119.713 |
| TIAMDGTEGLVR | 1261.40 | 1261.634 |
| ISVREPMQTGIK | 1357.70 | 1357.739 |
| IMNVIGEPIDER | 1384.68 | 1384.702 |
| AHGGYSVFAGVGER | 1405.66 | 1405.674 |
| FTQAGSEVSALLGR | 1434.73 | 1434.747 |
| TSIAIDTIINQKR | 1471.81 | 1471.836 |
| EAYPGDVFYLHSR | 1552.71 | 1552.731 |
| VALVYGQMNEPPGAR | 1600.79 | 1600.803 |
| TGAIVDVPVGEELLGR | 1623.87 | 1623.883 |
| LVLEVAQHLGESTVR | 1649.88 | 1649.910 |
| IMDPNIVGSEHYDVAR | 1814.85 | 1814.862 |
| VLDSGAPIKIPVGPETLGR | 1918.08 | 1918.089 |
| AIAELGIYPAVDPLDSTSR | 1986.99 | 1987.026 |
| IMNVIGEPIDERGPIKTK | 2009.10 | 2009.098 |
| IPSAVGYQPTLATDMGTMQER | 2265.06 | 2265.077 |
| EVAAFAQFGSDLDAATQQLLSR | 2337.15 | 2337.160 |

Binding of the Alpha-Subunit ATP Synthase Antibody to the Surface of HUVEC by Flow Cytometry and Immunofluorescence Microscopy.

To further confirm the surface localization of the ATP synthase, HUVEC were analyzed by flow cytometry and immunofluorescence microscopy. A rabbit polyclonal antiserum raised against the alpha subunit of ATP synthase from *E. coli* reacted with the cell membranes of HUVEC as determined by fluorescence-assisted flow cytometry (FIG. 4A). Control flow cytometry studies were performed by using A549 cells, which are known to express the alpha/beta-subunits of ATP synthase (Das, B., Mondragon, M. O. H., Sadeghian, M., Hatcher, V. B. & Norin, A. J. (1994) J. Exp. Med. 130, 273-281) (FIG. 4B). A549 cells also were analyzed with anti-alpha-subunit ATP synthase antibody pre-incubated with a 5-fold molar excess of recombinant alpha-subunit of ATP synthase protein and showed a decreased affinity for binding (FIG. 4C). HUVEC were incubated with increasing concentrations of antibody to determine saturation. FIG. 4D demonstrates specific, saturable binding of antibody directed against the alpha subunit of ATP synthase on HUVEC membranes.

Immunofluorescence microscopy of HUVEC confirmed the surface-associated immunoreactivity of alpha-subunit ATP synthase antibody on HUVEC cell membranes (FIG.

5A). Control experiments were performed with secondary antibody alone (FIG. 5D), pre-immune serum (FIG. 5E), and permeabilized HUVEC in the presence of anti-alpha-subunit ATP synthase antibody (FIG. 5F). Human dermal microvascular endothelial cells also reacted with antiserum raised against the alpha subunit of ATP synthase (FIG. 5C).

Inhibition of Angiostatin Binding in the Presence of the Antibody to the Alpha-Subunit of ATP Synthase.

The rabbit polyclonal antiserum raised against the alpha-subunit ATP synthase blocked binding of angiostatin to HUVEC by 59%, demonstrating that this protein functions in angiostatin binding (FIG. 6). In addition, $^{125}$I-labeled angiostatin bound to purified recombinant alpha subunit from human ATP synthase (FIG. 7B), and binding was inhibited ~56% in the presence of a 250-fold molar excess of unlabeled angiostatin (FIG. 7C). Complete inhibition of binding was not obtained and may be caused in part by nonspecific binding, improper folding of the recombinant protein, or binding epitopes only found in the presence of the alpha/beta-heterodimer. Furthermore, binding to the recombinant alpha subunit ATP synthase was not inhibited by a 2,500-fold molar excess of unlabeled plasminogen (FIG. 7D). $^{125}$I-labeled plasminogen did not bind to the recombinant alpha subunit of ATP synthase (FIG. 7E), but did bind to annexin II (FIG. 3D).

Inhibition of Proliferation in the Presence of Antibody to the Alpha-Subunit of Human ATP Synthase.

To determine whether the antiproliferative effects of angiostatin were mediated by ATP synthase binding, cell proliferation assays were performed in the presence of antiserum raised against the alpha subunit of ATP synthase from *E. coli*. The inhibitory effects of angiostatin on HUVEC proliferation were abrogated by approximately Si % in the presence of antibody to the alpha subunit of ATP synthase (Table 2), providing direct evidence that angiostatin binding to the alpha subunit of ATP synthase functions as a mechanism for inhibition of endothelial cell growth. These data indicated that this binding site could serve as a receptor for angiostatin.

TABLE 2

The antiproliferative effect of angiostatin is reversed by anti-alpha subunit ATP synthase antibody

| Concentration angiostatin added, μM | Percent proliferation inhibited, ±SEM | | % Recovery |
|---|---|---|---|
| | Without Antibody | With antibody | |
| 0 | 0 | 0 | 0 |
| 0.5 | 10 ± 1.4 | 1 ± 0.2 | 90 |
| 0.75 | 25 ± 4.2 | 5 ± 4.1 | 80 |
| 1.0 | 23 ± 9.0 | 6 ± 0.8 | 74 |

HUVEC were plated at a density of 5,000 cells/well in media containing angiostatin at a final concentration of 0.5, 0.75, and 1.0 mM. Anti-alpha-subunit ATP synthase antibody derived from *E. coli* was added concomitantly at a dilution of 1:100. MTS/PMS solution was added and absorbance of formazan was quantitated according to the manufacturer's specifications. Results represent three separate experiments performed in duplicate with SEM. Percent recovery represents the ability of the anti-alpha-subunit ATP synthase antibody to block the antiproliferative effect of angiostatin, and thereby restore proliferation to an average of 81% of that obtained with the control cells.

ATP synthase is composed of two functional domains termed F1 and F0. The F1 portion contains multiple subunits ($\alpha 3\beta 3\gamma\delta\epsilon$) and acts as the catalytic site for ATP synthesis, whereas the membrane-embedded F0 portion is a portion channel (Penefsky, H. S. & Cross, R. L. (1991) Adv. Enzymol. Relat. Areas Mol. Biol. 64, 173-214). Isolated alpha and beta subunits bind ATP and have weak ATPase activity; however, ATP synthesis requires all F1 sand F0 subunits (Boyer, P. D. (1997) Ann. Rev. Biochem 66, 717, 749).

Endothelial cells play a strategic role within the vasculature, serving as a barrier between the intravascular compartment and the underlying tissues, and often are exposed to hypoxic stress. Relative to other cell types, endothelial cells are more resistant to hypoxic challenge by their ability to maintain a high level of intracellular ATP (Graven, K. K. & Farber, H. W. (1997) Kidney Int. 51, 426-437). It is interesting to speculate that a plasma membrane-associated ATP synthase may produce extracellular ATP, which can diffuse back into the cell, providing an additional, albeit limited, ATP source (Unno, N., Menconi, M. J., Salzman, A. L., Smith, M., Hagen, S., Ge, Y., Ezzell, R. M. & Fink, M. P. (1996) Am. J. Physiol. 270, G1010-G1021; Unno, N., Menconi, M. J., Smith, M., Hagen, S. J., Brown, D. A., Aquirre, D. E. & Fink, M. P. (1997) Surgery 121, 668-680). Angiostatin, by binding to the alpha/beta-subunits of plasma membrane-localized ATP synthase, may disrupt this production of ATP, rendering endothelial cells more vulnerable to hypoxic challenge and eventual irreversible cell damage. In the microenvironment of a growing tumor, tissue hypoxia provides a powerful stimulus for the production of angiogenic growth factors such as vascular endothelial growth factor, basic fibroblast growth factor, and angiopoetin. The ability of host endothelial cells to respond to these growth factors by increased proliferation likely depends on their ability to survive hypoxic challenge. By abolishing the ability to resist low oxygen tension, angiostatin may decrease endothelial cell survival in the tumor microenvironment. It recently has been reported that angiostatin also may function by inducing endothelial cell apoptosis, providing an additional independent mechanism for the antiangiogenic action of this polypeptide (Claesson-Welsh, L., Welsh, M., Ito, N., Anand-Apte, B., Soker, S., Zetter, B., O'Reilly, M. & Folkman, J. (1998) Proc. Natl. Acad. Sci. USA 95, 5579-5583).

Binding of Antibody Directed Against the Alpha Subunit of ATP Synthase on the Surface of HUVEC by Flow Cytometry HUVEC cells were resuspended in ice-cold staining buffer (HBSS, 1% BSA, 0.1% sodium azide) and incubated on ice for 30 min with either rabbit polyclonal anti-serum raised against alpha subunit ATP synthase derived from *E. coli* or pre-immune rabbit serum. Cells were washed with ice-cold staining buffer and pelleted in a microfuge at 4° C. This wash was repeated twice and the cells resuspended in ice-cold staining buffer prior to incubation on ice for 30 min in the dark with goat anti-rabbit IgG conjugated to fluorescein isothiocyanate (FITC). Following the final wash (as above), the cells were pelleted and fixed in 10% neutral buffered formalin at a density of $1\times10^6$ cells/ml. Control experiments were performed using antibody directed against the alpha subunit of ATP synthase which was preincubated with a 5-fold molar excess of recombinant alpha subunit ATP synthase protein. The mean relative fluorescence following excitation at a wavelength of 488 nm was determined for each sample on a FACScan flow cytometer (Becton-Dickenson) and analyzed with CellQuest software (Becton-Dickenson). Histograms are shown in FIG. 8.

EXAMPLE 2

Demonstration that Endothelial Cell-surface $F_1$-$F_O$ ATP Synthase is Active in ATP Synthesis and is Inhibited by Angiostatin As discussed herein, angiostatin blocks tumor angiogenesis in vivo. This example demonstrates that $F_1$-$F_O$ ATP synthase is the major angiostatin binding site on the endothelial cell-surface, and this data suggests that ATP metabolism may play a role in the angiostatin response. The data also demonstrate that all components of the $F_1$ ATP synthase catalytic core are present on the endothelial cell surface, where they co-localize into discrete punctate structures. The surface-associated enzyme is active in ATP synthesis as shown by dual label thin layer chromatography and bioluminescence assays. Both ATP synthase and ATPase activities of the enzyme are inhibited by angiostatin as well as by antibodies directed against the alpha and beta subunits of ATP synthase in cell-based and biochemical assays. The data suggest that angiostatin inhibits vascularization by suppression of endothelial surface ATP metabolism, which in turn may regulate vascular physiology by established mechanisms. Antibodies directed against subunits of ATP synthase exhibit endothelial cell-inhibitory activities comparable to that of angiostatin, indicating that these antibodies function as angiostatin mimetics.

This example demonstrates conclusively that all components forming the core catalytic complex of $F_1$ ATP synthase are present on the external endothelial cell surface. Moreover, this enzyme is catalytically competent in the synthesis of ATP on the surface of endothelial cells. Finally, both angiostatin and antibodies against the alpha and beta subunits of ATP synthase inhibit activity of the surface-associated enzyme and of the purified enzyme. Taken together, these data strongly suggest that ATP synthase is the primary target for angiostatin on the surface of endothelial cells and further suggest that cell-surface ATP metabolism is likely to play a central role in the endothelial cell response to angiostatin. The ability of angiostatin or antibodies to disrupt ATP production renders endothelial cells more vulnerable to hypoxic challenge in the microenvironment of a growing tumor and additionally alters ATP-mediated signal transduction at the endothelial cell surface.

Materials and Methods

Confocal Microscopy. HUVEC were plated in EGM-MV media at 150,000 cells/ml on glass coverslips and allowed to adhere overnight. Cells were incubated at 4° C. and washed with PBS before fixation in 2% paraformaldehyde solution. A control slide was permeabilized in 100% ethanol for 5 min at rt before fixation. All coverslips were incubated in 5% goat serum in Dulbecco's PBS pH7.4 (Life Technologies, Gaithersburg, Md.) for 15 min and washed before co-incubation with murine monoclonal anti-alpha ATP synthase (Molecular Probes Inc., Eugene, Oreg.) (1:100) and rabbit polyclonal antibody raised against the recombinant human beta-subunit of ATP synthase (1:500) diluted in staining buffer (1% BSA/ 0.02% Tween 20/0.005M EDTA/1% goat serum/1XPBS, pH 7.4). To verify surface staining, cells were incubated with murine monoclonal anti-CD31 (PharMingen, Los Angeles, Calif.). All cells were washed three times and incubated for 1 hr in the dark at 4° C. with goat anti-mouse IgC AF488 F(ab')$_2$ (Molecular Probes) (1:100), goat anti-rabbit IgG AF546 F(ab')$_2$ (Molecular Probes) (1:200), or goat anti-mouse IgG1 AF633 (1:100) in staining buffer. After the final washes, cells were visualized using a Zeiss LSM-410 (Switzerland) confocal microscope at 630×.

ELISA Binding Studies. Binding studies were performed with purified $F_1$ subunit of bovine ATP synthase (20 g/ml) passively adsorbed onto polyvinylchloride microtiter 96-well flat bottom plates (Dynex Technologies, Inc, Chantilly, Va.) as previously described (22). Briefly, plates were coated with protein in 50 µl of 0.1M $Na_2CO_3$, pH9.6 and incubated 2 h at 37° C. Non-specific sites were blocked by incubating with PBS, pH 7.0 containing 1% BSA for 30 min at rt. Binding studies were performed with increasing amounts of angiostatin (0-0.5 mg/ml) added in a 50 l final volume for 1 h at 37° C. Plates were washed (0.1% Tween20/PBS, pH 7.0) and incubated with anti-human angiostatin antibody (goat IgG) (R&D Systems, Minneapolis, Minn.) (1:200 dil) overnight at 4° C. Plates were washed and incubated with anti-goat IgG peroxidase conjugate (Sigma. St. Louis, Mo.) (1:7500 dil) for 1 h at 37° C. Plates were washed and 150 µl of OPD substrate was added to each well and the reaction stopped with 25 µl of $H_2SO_4$ (25%), before monitoring the absorbance at $\lambda$=492 nm in a Molecular Devices SpectraMax Plus-384 plate reader. Control studies were performed in the absence of angiostatin to detect any non-specific binding of secondary proteins. Isotype specific controls were performed using a goat anti-fibronectin antibody (Sigma).

Purification of Bovine Heart $F_1$ ATP Synthase and $F_1$ Activity Assay. Fresh bovine heart mitochondria were obtained as previously described (23) and sonicated to yield sub-mitochondrial particles (24). The $F_1$ portion was separated from membrane-bound $F_O$ by chloroform extraction. The aqueous layer was centrifuged at 105,000×g to remove particulate matter before purifying over an S300 gel filtration column. The purified $F_1$ ATP synthase only exhibits activity in the reverse reaction (ATPase), because the forward reaction (ATP synthase) requires the $F_1$-$F_O$ holoenzyme correctly assembled into a membrane across which a proton gradient exists. ATPase activity was measured spectrophotometrically by monitoring at $\lambda$=340 nm by coupling the production of ADP to the oxidation of NADH via pyruvate kinase and lactate dehydrogenase reactions as described in Zheng, & Ramirez, *Biochem Biophys Res Commun* 261(25):499-503 (1999).

Cell-surface ATP Assay. Quiescent, confluent HUVEC in 24 well plates were washed and equilibrated into DMEM/F-12 (HAM) 1:1 medium (Life Technologies) containing 10 mM potassium phosphate. Cells were treated with (1 µM) angiostatin or (0.1 mg/mL) oligomycin for 1 hr at 37° C. All cells were then incubated with 0.1 Ci $^{32}$P and 0.1 Ci (50 M) [2,8-$^3$H]-ADP (NEN Life Sciences) for 1 min. Supernatants were removed and centrifuged before assaying for ATP production by thin layer chromatography (TLC) or by firefly luciferase assay.

ATP Generation by Bioluminescent Luciferase Assay. Aliquots (50 µl) of cellular supernatants from cell-surface ATP assays were analyzed using the ATP bioluminescence assay kit (Sigma Chemical, St. Louis, Mo.). In this firefly luciferin-luciferase reaction, only ATP is readily detected since the enzymatic reaction of firefly luciferase to oxidize luciferin is specific for ATP relative to all other nucleotides. Samples were injected with the ATP assay mixture and recordings were made in a LuminoskanRS (LabSystems, Franklin, Mass.) over a 10 s period. The response in a given sample or standard was quantified as area under the peak of the response and averaged for duplicate determinations. Data are expressed as picomoles of ATP produced per cell based on standards determined under the same conditions with each experiment. Angiostatin was prepared as described in Sottrup-Jensen, L., Claeys, H., Zajdel, M., Petersen, T. E. & Magnusson, S. (1978) *Progress in Chemical Fibrinolysis and Thrombolysis* (Raven Press, New York). Angiostatin did not interfere with the luciferin-luciferase assay, indicating that the effects of angiostatin are not an assay artifact (data not shown).

Dual Label Radioactive Thin Layer Chromatography of ATP. Supernatants were obtained as described above. Cell pellets were obtained after washing wells with 1.0 ml media (as described above) and lysing with 1N NaOH (100 µl 1).

Aliquots of supernatant (3 1) and cell pellet (10 µl) were applied to microcrystalline cellulose PEI plates (Anal. Tech., Newark, Del.) along with an authentic [$^{32}$P]ATP standard (0.025 Ci). Plates were developed in 1.4 M LiCl for a distance of 15 cm. Dried spots containing [$^{32}$P]ATP, [$^3$H]ATP, and [$^3$H]ADP were detected by sodium iodide and phosphoimaging on a STORM 850 (Molecular Dynamics, Sunnyvale, Calif.). Areas corresponding in $R_f$ value to co-chromatographed authentic [$^{32}$P]ATP standard were scraped off the plate and their radioactivity determined in a liquid scintillation analyzer (Packard BioScience Co., Meridan, Conn.). No ATP was detectable by TLC in the [$^3$H]ADP preparation used for all experiments.

Cell Proliferation Assay. HUVEC were plated at a density of 5000 cells/well in media depleted of fetal calf serum (FCS) overnight to allow the cells to become quiescent. Fresh media containing 5% FCS, 10 ng/ml basic fibroblast growth factor (bFGF) and 3 ng/ml vascular endothelial growth factor (VEGF) were added to the wells along with angiostatin (1.0 µM), antibody directed against the recombinant human alpha-subunit of ATP synthase (1:10 dil), antibody directed against the recombinant human beta-subunit of ATP synthase (1:10 dil), pre-immune serum (1:10 dil) or cycloheximide (10 g/ml). Cell density was measured after 24 hrs using CyQUANT Cell Proliferation Assay Kit (Molecular Probes) in a fluorometric plate reader (Molecular Devices). The absorbance values used to calculate the percent proliferation of the cells ranged from 1.24 or 1.00 for treated and 2.57 for untreated.

Results: Alpha and Beta-subunits of ATP Synthase Co-Localize on the Surface of HUVEC.

Extensive co-localization of the alpha- and beta-subunits of ATP synthase on the endothelial cell surface is demonstrated using confocal microscopy with a monoclonal antibody specific for the alpha-subunit of ATP synthase and affinity-purified antibodies generated against the recombinant beta-subunit of ATP synthase (FIG. 9C). The immunofluorescence occurs in two distinctive patterns. First, there are numerous fine punctate structures distributed over the entire cell surface, except where the bulging nucleus displaces the plasma membrane from the optical section. Second, each cell displays one or more irregular clusters of punctate structures, suggesting an organized distribution on the cell surface. The cells were fixed in situ prior to addition of antibodies to eliminate antibody-capping artifacts. Parallel studies of immunolocalization between the alpha- and gamma-subunits of ATP synthase showed virtually identical patterns of co-localization (data not shown).

Fluorescence in all images was determined to be cell-surface associated by three criteria: 1) permeabilized cells (FIG. 9D) produced a dramatically different pattern characteristic of mitochondrial staining of ATP synthase. Endothelial cell mitochondria are characteristically tubular and reticular in pattern, with a peri-nuclear concentration as seen in Panel D. 2) Confocal optical sectioning along the z-axis confirmed an apical concentration of antigen distribution characteristic of surface staining (FIG. 10 A-D, discussed below). 3) Co-staining with a known endothelial cell-surface marker, CD31, produced overlapping distributions in z-axis optical sections, as would be expected for surface localization (FIG. 10 C). Flow cytometry of primary HUVEC was also performed with cells determined to be non-permeabilized by dye exclusion. These cells demonstrated cell surface expression of the alpha-subunit of ATP synthase (data not shown) confirming that the staining of ATP synthase that we detect is not due to permeabilization but rather to the presence of this enzyme on the cell surface.

The cell surface localization was further investigated by confocal microscopy comparing staining with CD31, an established endothelial cell surface marker, and the alpha-subunit of ATP synthase. Additional confocal micrographs (not shown) were taken where the fluorescence from the red channel and from the green channel only were used. These micrographs demonstrate CD31 and α-ATP synthase staining, respectively, while panel C shows the overlay of these two images. The image in panel C was taken at approximately the midpoint between the basal and apical surfaces of cultured endothelial cells and clearly shows a marginal distribution of the punctate structures containing ATP synthase along the periphery of the cells. Panels A-D show the same field of view in optical sections along the z-axis, with A starting near the basal aspect and D ending near the apical aspect of the cultured cells. It is important to note that the apical surface would be equivalent to the lumenal surface if these cells were within the vasculature. Although confocal microscopy emphasizes structures within the optical plane of sectioning, structures that are above or below the plane of section may also be visualized if their staining is particularly intense. However, structures that are outside the confocal plane will display fuzzy margins, while structures within the focal plane will show sharp margins. This effect is seen with the α-ATP synthase staining. Examination of the sharp green spots demonstrates that essentially all α-ATP synthase staining is confined to the cellular margins in subapical sections of non-permeabilized cells (Panels A-C). Moreover, α-ATP synthase exhibits a greater intensity of staining in the apical section (Panel D), in which the confocal plane grazes the majority of the exposed apical surface, as would be expected for a surface-localized marker.

Angiostatin Binds to Bovine $F_1$ ATP Synthase. Human angiostatin bound to purified bovine $F_1$ ATP synthase passively adsorbed onto micro-titer wells in a concentration-dependent manner (FIG. 11). Human and bovine ATP synthase are highly homologous, differing only by 8 amino acid residues in the mature α-chains (SWISS-PROT accession numbers P25705 and P19483, respectively) and 6 residues in the mature β-chains (SWISS-PROT accession numbers P06576 and P00829, respectively). Similar results were obtained with purified bovine $F_1$ ATP synthase binding to immobilized angiostatin (data not shown). Microtiter wells coated with decreasing concentrations of purified bovine $F_1$ ATP synthase also showed concentration-dependent binding of angiostatin (data not shown). Background binding of angiostatin to BSA-coated wells gave values comparable to the baseline seen in FIG. 11 (compare 0 µg/ml to 0.2 µg/ml), indicating that angiostatin requires $F_1$ ATP synthase for efficient binding. Apparent dissociation constants ($K_{d(app)}$) were determined from double reciprocal plots of the binding data as shown on the inset of FIG. 11. The $K_{d(app)}$ for angiostatin binding to purified $F_1$ ATP synthase is 12 nM. The holoenzyme associates with numerous other proteins on the cell surface and thus may be sterically hindered to a significant degree. In contrast, the purified $F_1$ subcomplex would not be subjected to steric hindrance by associated proteins and would be expected to exhibit an increased affinity for its ligands.

Angiostatin Inhibits Purified Bovine $F_1$ ATP Synthase Activity. Although the $F_1$-$F_O$ ATP synthase holoenzyme efficiently catalyzes both the forward ATP synthase reaction and the reverse ATP hydrolysis reaction, the purified $F_1$ ATP synthase sub-complex only catalyzes the reverse reaction. The ATP hydrolytic activity of the purified bovine $F_1$ ATP synthase was measured using a coupled enzymatic assay in which production of ADP is linked to oxidation of NADH via pyruvate kinase and lactate dehydrogenase, as shown in Zheng, J. & Ramirez, V. D. (1999) *Eur J Pharmacol* 368, 95-102. Thus, a decrease in the absorbance measured at λ=340 nm indicates ATPase activity. Angiostatin completely inhibited purified ATPase activity, similar to a known $F_1$ inhibitor, $NaN_3$ (FIG. 12). Polyclonal antibodies directed against the recombinant alpha-, beta-, and gamma-subunits of ATP synthase were also tested. Both alpha- and beta-subunit-specific ATP synthase polyclonal antibodies abolished ATPase activity. In contrast, the gamma-subunit-specific ATP synthase antibody had no effect (data not shown). In addition, a commercial monoclonal antibody specific for the alpha-subunit of ATP synthase (Molecular Probes) also inhibited activity. Pre-immune, unrelated polyclonal, and unrelated monoclonal antibodies employed as controls had no effect on activity.

Surface-Associated ATP synthase is Catalytically Competent. The presence of the alpha, beta and gamma-subunits of ATP synthase on the endothelial cell surface suggests that the entire catalytic complex is present. To test for functional activity, we incubated HUVEC with [$^3$H]ADP, [$^{32}$P$_i$] and unlabeled phosphate (100 mM), and followed ATP production by analysis of supernatants on microcrystalline cellulose PEI TLC plates. ATP generation was detected within the first 15 s and reached maximal levels by 1 min. The possibility of ATP release from intracellular pools was discounted because the cells tested were intact as evident by Trypan blue exclusion and lack of LDH release (data not shown). Moreover, the ratio of [$^3$H]ATP/[$^{32}$P]ATP remained constant at 1.56+/–0.04 over the time measured, thus demonstrating that the ADP and $P_i$ substrates used to form ATP were derived exclusively from the external medium. No labeled product was detectable within the cell pellets (data not shown) again confirming that the ATP was synthesized on the cell surface.

To determine whether angiostatin inhibits ATP synthesis on the endothelial cell surface, ATP production in the extracellular medium was measured using a bioluminescence assay. This assay is highly specific for ATP, to the exclusion of all other nucleotides. ATP concentrations significantly above basal levels were detected in the extracellular milieu, indicating that de novo ATP synthesis occurred on the cell surface (Table 3). Release of intracellular ATP pools was excluded by the low level of ATP measured in the absence of ADP. Angiostatin inhibited ATP synthesis in a dose-dependent manner (FIG. 13). ATP synthesis was inhibited 81% by 1 μM angiostatin as shown in Table 3.

TABLE 3

Inhibition of ATP Generation on the Surface of HUVEC as Measured by Bioluminescent Luciferase Assay*

| Treatment applied to cultured HUVEC in the presence of 50 μM ADP | Percent Inhibition (+/–S.E.M.) |
|---|---|
| Medium alone | 0 |
| Angiostatin (1 μM) | 81 +/– 6/0 |
| Polyclonal alpha-ATP synthase (1.0 mg/ml) | 64.8 +/1 3.2 |
| Polyclonal beta-ATP synthase (0.5 mg/ml) | 56.8 +/– 5.8 |
| Pre-immune serum (1.0 mg/ml) | 0 +/– 7.6 |
| Oligomycin | 83.5 +/– 4.5 |

*Basal ATP levels in the assay medium (in the absence of ADP) produced bioluminescence signals equivalent to approximately 4% of the uninhibited levels in the presence of ADP.

Polyclonal antibodies against either the alpha or beta-subunits of ATP synthase inhibited cell-surface production of ATP by 65% and 57%, respectively. In contrast, pre-immune serum showed no inhibition. Oligomycin, a known inhibitor of the $F_O$ sub-complex, inhibited ATP synthesis by 84% under these conditions, confirming that the major activity assayed was due to ATP synthase.

Inhibition of HUVEC Proliferation in the Presence of Angiostatin and anti-ATP Synthase Antibodies. Polyclonal antibodies raised against the beta-subunit of ATP synthase inhibited endothelial cell proliferation 1.5-2-fold more effectively than angiostatin itself (Table 4).

TABLE 4

Inhibition of HUVEC Proliferation in the presence of Angiostatin and anti-betaATP Synthase antibody as Measured by CYQUANT

| | Percent Inhibition (+/–S.E.M.) |
|---|---|
| Medium alone | 0 +/– 1.034 |
| Angiostatin (1 μM) | 57.2 +/– 1.16 |
| Cycloheximide (10 μg/ml) | 100 +/– 7.0 |
| Polyclonal beta-ATP synthase (100 μg/ml) | 80.9 +/– 15.9 |
| Pre-immune serum (100 μg/ml) | 0 +/– 1.7 | n=3

The antiproliferative effect of the beta-subunit-specific antibody approached that of cycloheximide (80.9% and 100%, respectively). However, this effect is unlikely to represent a toxic response since the cellular morphology of the anti-beta-subunit ATP synthase treated cells was unchanged from that of untreated cells, in contrast to the obvious rounded morphology caused by cycloheximide (data not shown). The preimmune serum exhibited no effect on proliferation. These data suggest that antibodies directed against the beta-subunit of ATP synthase act as angiostatin mimetics in both biochemical and cell-based assays of ATP synthase function.

Discussion

This study demonstrates that ATP synthase is catalytically active on the endothelial cell surface and that angiostatin-mediated inhibition of this activity correlates with inhibition of proliferation. Moreover, certain antibodies directed against the alpha and beta-subunits of ATP synthase also inhibit enzymatic activity and endothelial cell proliferation. These antibodies, therefore, appear to constitute functional mimetics of angiostatin.

In addition to angiostatin, there are known inhibitors of ATP synthase that exhibit anti-tumor effects including piceatannol and resveratrol. Resveratrol inhibits the development of DMBA-induced preneoplastic lesions and tumor growth (30). Piceatannol was shown to inhibit tumor cell growth by inhibition of protein-tyrosine kinases. The fact that both of these anti-tumor compounds inhibit ATP synthase suggests a relationship between the endothelial cell antiproliferative effects of angiostatin and cell-surface associated ATP synthesis.

The generally accepted concept that ATP synthesis is strictly an intracellular process now appears questionable. It is well established that both nucleosides and nucleotides act as extracellular signaling molecules. Indeed, the extracellular role of nucleotides in regulating multicellular communication is widely conserved in eukaryotic evolution. Extracellular receptors for ATP exist as both ion channels (P2X) and G-protein coupled receptors (P2Y) that are ubiquitous to all mammalian tissues. A recent study demonstrates that ATP release by physical or chemical means contributes to the set point of cellular signaling pathways coupled to P2Y receptors (Ostrom, R. S., Gregorian, C. & Insel, P. A. (2000) *J Biol Chem* 275, 11735-9). In the cardiovascular system, adenosine released from myocytes maintains blood flow to ischemic areas of the heart, and ATP may play a role in the moment-to-moment regulation of cardiac blood flow in non-pathological states. Endothelial cells release ATP in response to stimuli such as shear stress and vasoactive agonists including ATP itself.

The immunolocalization data show that the alpha, beta and gamma-subunits of ATP synthase are present on the endothelial cell surface where they extensively co-localize. These subunits represent the minimal components required for efficient ATPase catalytic activity and strongly suggest that the cell-surface form of ATP synthase is similar to the mitochondrial form. Moreover, cell-surface ATP synthase is present in discrete foci, indicating structural organization of the enzyme complex. Numerous other mitochondrial matrix enzymes that co-localize with ATP synthase into these discrete foci on the endothelial cell surface were also detected, but mitochondrial outer membrane markers were not detected (data not shown). These findings suggest that a highly complex energy production apparatus exists on the endothelial cell surface.

The data strongly suggest that angiostatin operates through inhibition of the enzymatic activity of cell-surface ATP synthase. Data supporting this interpretation include concordance of inhibitory activities of angiostatin, known small molecule inhibitors of ATP synthase, and antibodies specific for ATP synthase subunits in binding and biochemical assays using purified bovine enzyme. There are also similar effects of angiostatin and subunit-specific antibodies in inhibition of ATP production on the surface of cultured human endothelial cells. It should be noted that existing small molecule inhibitors cannot be used in this assay because they also inhibit the mitochondrial form of ATP synthase, whereas neither angiostatin nor the subunit-specific antibodies cross the cell membrane. Finally, angiostatin and anti-beta-subunit antibodies show similar ability to inhibit proliferation of cultured human endothelial cells.

Collectively, these data suggest a steric hindrance model of ATP synthase inhibition by angiostatin. ATP synthase couples proton flux across a membrane to rotation of the gamma-subunit, which in turn induces cyclical conformational changes in the catalytic beta-subunit Boyer, P. D. (1997) *Annu Rev Biochem* 66, 717-49. These conformational changes, required for conversion of ADP to ATP, can be blocked by any compound that either inhibits rotation of the gamma-subunit or locks the conformation of the alpha or beta-subunits. The binding of specific antibodies can lock the conformation of flexible antigens. Thus, both angiostatin and certain antibodies to the alpha or beta-subunits of ATP synthase inhibit the enzyme by blocking conformational changes of the enzyme complex required for ATP synthesis or hydrolysis. Functional mimetics of angiostatin can be derived by developing monoclonal antibodies against the alpha or beta-subunits of ATP synthase. Such antibodies will be far easier to produce and administer than angiostatin and offer significant advances in anti-angiogenic therapy of cancer and other proliferative diseases.

All documents cited above are hereby incorporated in their entirety by reference. From the foregoing, it will be obvious to those skilled in the art that various modifications in the above-described methods, and compositions can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the claims are therefore intended to be embraced therein.

We claim:

1. A method of inhibiting the binding of angiostatin to the alpha or beta subunits of human F1 ATP synthase on endothelial cells, comprising administering to a subject in need thereof an antibody or an antigen-binding antibody fragment thereof in an amount effective to inhibit the binding of angiostatin to the alpha or beta subunits of F1 ATP synthase F1 ATP synthase, wherein the antibody or antigen-binding antibody fragment binds to the alpha or beta subunit of F1 ATP synthase and is an angiostatin agonist.

2. The method of claim 1, wherein the antibody or antigen-binding antibody fragment thereof is a monoclonal antibody or binding fragment thereof.

3. The method of claim 1, wherein the antibody or antigen-binding antibody fragment thereof is a humanized antibody or binding fragment thereof.

4. The method of claim 1, wherein the antibody or antigen-binding antibody fragment is present in or conjugated onto a liposome or microparticle.

5. The method of claim 1, further comprising administering a COX-2 inhibitor.

6. The method of claim 1, wherein the antibody or antigen-binding antibody fragment is administered intravenously, intramuscularly, intradermally or subcutaneously.

* * * * *

UNITED STATES PATENT AND TRADEMARK OFFICE
CERTIFICATE OF CORRECTION

PATENT NO. : 8,048,415 B2  Page 1 of 1
APPLICATION NO. : 12/538952
DATED : November 1, 2011
INVENTOR(S) : Moser et al.

It is certified that error appears in the above-identified patent and that said Letters Patent is hereby corrected as shown below:

Column 6, Line 61: Please correct "$(\alpha_3\beta_3\gamma\delta\epsilon)$" to read -- $(\alpha_3\beta_3\gamma\delta\varepsilon)$ --

Column 7, Line 10: Please correct "The β-subunits" to read -- The α-subunits --

Column 33, Line 19: Please correct "100 mM $\epsilon$-aminocaproic"
to read: -- 100 mM ε-aminocaproic --
Line 37: Please correct "100 mM $\epsilon$-aminoca5proic"
to read: -- 100 mM ε-aminocaproic --

Column 36, Line 12: Please correct "as annexin H." to read -- as annexin II. --

Column 37, Line 66: Please correct "$(\alpha3\beta3\gamma\delta\epsilon)$" to read -- $(\alpha3\beta3\gamma\delta\varepsilon)$ --

In the Claims:
Column 46, Claim 1, Line 28: Please correct "F1 ATP synthase"
to read -- F1 ATP synthase, --
Line 29: Please delete "F1 ATP synthase,"

Signed and Sealed this
Twenty-seventh Day of November, 2012

David J. Kappos
*Director of the United States Patent and Trademark Office*